US009289307B2

(12) United States Patent
Shohat

(10) Patent No.: US 9,289,307 B2
(45) Date of Patent: Mar. 22, 2016

(54) PROSTHETIC DEVICES AND METHODS FOR USING SAME

(71) Applicant: Ortho-Space Ltd., Caesarea (IL)

(72) Inventor: Shaul Shohat, Kfar HaOranim (IL)

(73) Assignee: Ortho-Space Ltd., Caesarea (IL)

( * ) Notice: Subject to any disclaimer, the term of this patent is extended or adjusted under 35 U.S.C. 154(b) by 0 days.

(21) Appl. No.: 14/352,614

(22) PCT Filed: Oct. 18, 2012

(86) PCT No.: PCT/IB2012/002088
§ 371 (c)(1),
(2) Date: Apr. 17, 2014

(87) PCT Pub. No.: WO2013/057566
PCT Pub. Date: Apr. 25, 2013

(65) Prior Publication Data
US 2014/0371864 A1    Dec. 18, 2014

Related U.S. Application Data

(60) Provisional application No. 61/548,232, filed on Oct. 18, 2011.

(51) Int. Cl.
*A61F 2/40* (2006.01)
*A61B 17/56* (2006.01)
*A61F 2/02* (2006.01)
*A61F 2/08* (2006.01)
*A61F 2/30* (2006.01)

(52) U.S. Cl.
CPC ............ *A61F 2/4081* (2013.01); *A61B 17/562* (2013.01); *A61F 2/02* (2013.01); *A61F 2002/087* (2013.01); *A61F 2002/30579* (2013.01); *A61F 2002/30581* (2013.01); *A61F 2002/30754* (2013.01); *A61F 2250/0003* (2013.01)

(58) Field of Classification Search
CPC ............ A61F 2/40; A61F 2002/30581; A61F 2002/30583; A61F 2/441
See application file for complete search history.

(56) References Cited

U.S. PATENT DOCUMENTS

| 5,658,324 | A  * | 8/1997  | Bailey et al. ................. 607/104 |
| 2004/0254625 | A1 | 12/2004 | Stephens et al. |
| 2007/0038292 | A1 | 2/2007 | Danielpour |
| 2007/0078477 | A1 | 4/2007 | Heneveld et al. |
| 2009/0048683 | A1 * | 2/2009 | Morris et al. ............. 623/23.48 |
| 2010/0023127 | A1 | 1/2010 | Shohat |
| 2012/0165941 | A1 * | 6/2012 | Rabiner et al. ............ 623/17.12 |

OTHER PUBLICATIONS

International Search Report issued in connection with International Application No. PCT/IB2012/002088 dated Mar. 1, 2013.

* cited by examiner

*Primary Examiner* — Yashita Sharma
*Assistant Examiner* — Daniel Bissing
(74) *Attorney, Agent, or Firm* — Fish & Richardson P.C.

(57) ABSTRACT

In one embodiment, the instant invention is a method that includes at least providing a prosthesis that includes at least an implant capable of deformation under pressure; inserting the implant in a void space in a joint; inflating the implant by adding a first amount of a filler to the implant, where the first amount of the filler is X; articulating the joint; releasing a second amount of the filler from the implant through a pressure regulating valve based on a predetermined pressure in the implant, where the second amount of the filler released from the implant is Y; and sealing the implant, where X is greater than Y.

17 Claims, 9 Drawing Sheets

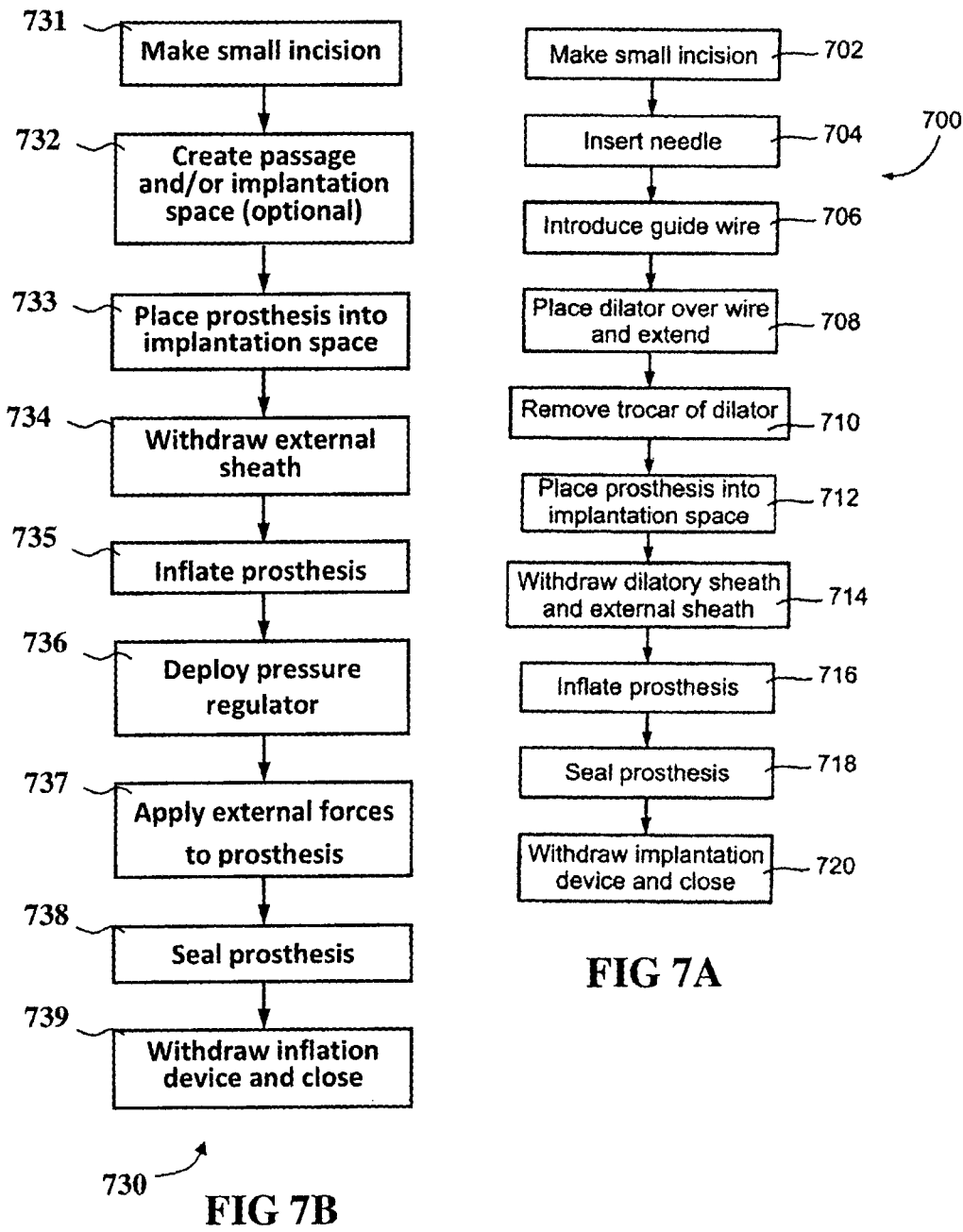

PROSTHETIC DEVICES AND METHODS FOR USING SAME

CROSS-REFERENCE TO RELATED APPLICATIONS

The present application is a national phase filing under 35 USC 371 of International Application No. PCT/IB2012/002088, filed on Oct. 18, 2012, which claims the benefit of U.S. provisional patent application No. 61/548,232, filed on Oct. 18, 2011, the disclosures of both of which are incorporated herein by reference.

FIELD OF INVENTION

The present inventions relate generally to the field of medical devices and the treatment of human medical conditions using the medical devices. More specifically, the present inventions include expandable prosthetic devices used for treating a variety of conditions, including rotator cuff injuries, broken and/or depressed bone fractures, infection and/or inflammation in the body.

BACKGROUND OF THE INVENTION

Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues.

Severe or complete tears and deterioration of articulations (i.e., bodily joints) related tissues (such as tendons, ligaments, capsules, cartilage and bony parts), and other bodily elements (such as bursae, synovium and other membranes) may cause severe pain, hindered movement up to complete disability, joint parts dislocation, and other possible phenomena.

Some joints related deteriorations can be amended by filling voids and spaces between tissues with volumetric fillers especially in scenarios where there is a need to create or revive unhindered relative motion between such tissues. Such volumetric fillers should possess specific combined characteristics such as 3D geometry, external surface texture and overall consistency in order to avoid inefficacy on the one hand and stiff sensation on the other. Since that patients differ much on such voids geometries, mechanical and physical properties of voids' boundaries, and overall shoulder consistency, weight and strength, it is therefore needed that the volumetric fillers will be patient-specific in the sense that it will be deployed, shaped and fine-tuned in-vivo.

SUMMARY OF THE INVENTION

In some embodiments, the present invention includes a method of implanting a prosthesis in a body that includes at least the following steps: providing a prosthesis that includes at least an implant capable of deformation under pressure; inserting the implant in a void space in a joint; inflating the implant by adding a first amount of filler to the implant where the first amount of filler is X; articulating the joint; releasing a second amount of filler from the implant where the second amount of filler released from the implant is Y; and sealing the implant where X is greater than Y. In some embodiments, inflating the implant by adding a first amount of filler causes the implant to fully expand, fully unroll, and/or expand a void to a predetermined shape and/or size.

In some embodiments, the articulating the joint step and the releasing a second amount of filler from the implant where the second amount of filler released from the implant is Y step occur concomitantly. In some embodiments, the releasing a second amount of filler from the implant where the second amount of filler released from the implant is Y step is caused by the articulating the joint step.

In some embodiments, the method include the implant having a first face and an opposing second face, where the method further includes articulating the joint to result in a predetermined distance between the first face of the implant and the opposing second face of the implant, where the predetermined distance between the first face of the implant and the opposing second face of the implant is greater than 0 millimeters.

In some embodiments, the ratio of X:Y is less than or equal to 4:1. In some embodiments, the ratio of X:Y is less than or equal to 2:1. In some embodiments, the ratio of X:Y is less than or equal to 1.3:1.

In some embodiments, the implant is a bladder. In some embodiments, the implant is formed of a biodegradable material. In some embodiments, the implant is formed of a biodegradable material that may include polycaprolactone, polyglycolide, polyhydroxybutyrate, plastarch material, polyetheretherketone, zein, polylactic acid, polydioxanone, poly(lactic-co-glycolic acid), poly(lactice acid-co-epsilon caprolactone), collagen, and/or methyl cellulose.

In some embodiments, the joint is a mammalian joint. In some embodiments, the joint is a shoulder joint.

In some embodiments, the filler includes at least a biocompatible fluid. In some embodiments, the filler includes at least a biocompatible fluid that is saline.

In some embodiments, the method includes a step of inflating the implant sufficiently to contact at least one surface of a tissue in the joint.

In some embodiments the method includes articulating the joint that includes at least a forward flexion, an abduction, an external rotation, an internal rotation and/or a cross-body adduction.

In some embodiments, the present invention includes a method of implanting a prosthesis in a body that includes at least the following steps: providing a prosthesis that includes at least an implant capable of deformation under pressure; inserting the implant in a void space in a joint; inflating the implant by adding a first amount of a filler to the implant, where the first amount of the filler is X; articulating the joint; releasing a second amount of the filler from the implant through a pressure regulating valve based on a predetermined pressure in the implant, where the second amount of the filler released from the implant is Y; and sealing the implant, where X is greater than Y. In some embodiments, the joint is a shoulder joint.

In some embodiments, the implant includes the pressure regulating valve. In some embodiments, the pressure regulating valve is external from the implant.

In some embodiments, the predetermined pressure in the implant is at least 8 pounds per square inch. In some embodiments, the predetermined pressure in the implant is at least 12 pounds per square inch. In some embodiments, the predetermined pressure in the implant is at least 20 pounds per square inch.

In some embodiments, the method further includes releasing filler from the implant into the void space in the joint.

In some embodiments, the articulating the joint step and the releasing a second amount of filler from the implant through a pressure regulating valve based on a predetermined pressure in the implant, where the second amount of filler released from the implant is Y step occur concomitantly. In some embodiments, the releasing a second amount of filler from the implant through a pressure regulating valve based on a predetermined pressure in the implant, where the second amount of filler released from the implant is Y step is caused by the articulating the joint step.

In some embodiments, the ratio of X:Y is less than or equal to 2:1.

In some embodiments, the present invention is a prosthesis having an implant having a pressure regulating valve, where the implant is capable of being positioned between a first tissue and an opposing second tissue in a joint, where the implant is capable of deforming under pressure in response to articulation of the joint, and where the pressure regulating valve is configured to open based on a predetermined pressure in the implant.

In some embodiments, the implant is a fluid filled bladder. In some embodiments, the pressure regulating valve is configured to open based on a predetermined pressure of 8 pounds per square inch. In some embodiments, the fluid filled bladder is filled with saline. In some embodiments, the implant and/or the pressure regulating valve are formed of a biodegradable material.

In some embodiments, the filler includes at least a biocompatible fluid. In some embodiments, the filler includes at least a biocompatible fluid that is saline. In some embodiments, the pressure regulating valve is formed of a biodegradable material.

In an aspect of some embodiments, there is provided a prosthesis use in a mammalian joint. In some embodiments, the prosthesis includes an implant configured for spacing the tissue associated with articulation away from adjacent tissue. In some embodiments, the implant is capable of being deforming to accommodate for pressure applied thereupon by the tissue associated with articulation and/or the adjacent tissue. In some embodiments, the implant is subject to viscoelastic deforming or resembling viscoelastic-like behavior. Optionally, the implant is formed from a biodegradable material.

In some embodiments, the pressure applied to the implant results from movement of tissue associated with articulation and/or the adjacent tissue. Optionally, the implant is sized and configured for a rotator cuff tissue.

In some embodiments, the implant is a fluid filled bladder, optionally partially filled, optionally filled with saline. In some embodiments, the deforming does not result in a substantial increase in stress on a wall of the bladder. In some embodiments, the bladder is formed from a non-compliant or a semi-compliant material. In some embodiments, an internal fluid pressure of the fluid filled bladder does not rise above 8 PSI during the deforming.

In some embodiments, the fluid filled bladder includes a valve for regulating a fluid pressure within the bladder. The valve may be configured for releasing fluid out of the fluid filled bladder above a predetermined internal fluid pressure, optionally 8 psi. Optionally, the valve is biodegradable. In some embodiments, a system is provided comprising the implant and an inflation apparatus detachably coupled to the bladder.

In an aspect of some embodiments, there is provided a prosthesis for use in the articulation of a mammalian joint comprising an implant configured for providing floatation-like support to the tissue associated with articulation thereby minimizing interface pressure and friction on tissue associated with articulation.

Also provided, in accordance with some embodiments of the invention, is a method of implanting a prosthesis configured for use in the articulation of a mammalian joint. In some embodiments, the method includes implanting the prosthesis in contact with the tissue associated with articulation, and articulating the joint, thereby enabling the prosthesis to deform and accommodate for pressure applied thereupon by the tissue associated with articulation and/or adjacent tissue.

In some embodiments, the tissue associated with articulation is a rotator cuff tendon, a humerus, an acromion or a coracoid process.

In some embodiments, the method further includes measuring a natural void between a limb bone and an adjacent trunk bone surrounding the joint and selecting the prosthesis according to a size and/or shape of the void. Optionally, the limb bone is a humerus and the trunk bone is an acromion or a glenoid.

In some embodiments, the prosthesis is a fluid expandable bladder and the method includes expanding the prosthesis to a first size and/or a shape prior to articulation the joint. Optionally, joint articulation results in deformation of the prosthesis to a second size and/or a shape. The second size and/or the shape may result from release of fluid from the bladder. Optionally, the bladder is sealed at the second size and/or the shape.

In some embodiments, articulating the joint is through a full range of motion, optionally a passive range of motion, optionally any of a forward flexion, an abduction, an external rotation, an internal rotation and a cross-body adduction.

In some embodiments, the method further includes debriding tissues in the natural void. Optionally, the method further includes fixating the prosthesis in position.

In some embodiments, the bladder includes at least one smooth surface and the second size and/or the shape impose a predetermined friction characteristic between the at least one smooth surface and the tissue associated with articulation. Optionally, the friction characteristic is at least one of a static dry friction force, a kinetic friction force, a friction coefficient and a normal force applied to the tissue type in continuous contact with the smooth surface. Optionally, the friction characteristic allows a chosen transient between a static friction force and a kinetic friction force, thereby allowing movement of the prosthesis in a stable equilibrium positioning.

In an aspect of some embodiments, the prosthesis includes a tissue positioning device, comprising: a biocompatible member having a size and shape suitable for placement within a space adjacent to a tissue to be positioned, the tissue forming a portion of an articulatable joint; such that, when placed within the space, the member acts to maintain the tissue in a desired position. Optionally, the member is a spacer which has a defined shape when acting to maintain the tissue in the desired position. Optionally, the member arranged such that its size and shape are suitable for placement within a given space and for positioning a particular tissue. In some embodiments, the member comprises: a bladder having an associated deflated state and which is capable of receiving and being at least partially expanded by a filler material; and a valve by which a filler material can be delivered into the bladder; such that the bladder is capable of insertion into the space when in the deflated state and acts to maintain the tissue in the desired position when at least partially expanded by the delivery of filler material via the valve. Optionally, the tissue is hard or soft tissue. Optionally, the space is between the acromium, deltoid muscle, and humerus, such that, while placed within the space, the member acts to maintain the head of the humerus within the cup of the glenoid.

An aspect of some embodiments of the invention relates to prostheses adapted to reduce injuries between soft tissues of the body and other tissues. In an embodiment of the invention, soft tissues are for example, tendons and/or ligaments. In an embodiment of the invention, other tissues are, for example, bones. In an embodiment of the invention, the prosthesis is expandable. Optionally, the prosthesis is elastic. In some embodiments of the invention, the prosthesis is rigid. In an embodiment of the invention, the prosthesis is shaped and/or sized to simulate a bursa naturally occurring in the body. Optionally, the bursa simulated is the one expected to be present at the implantation site of the prosthesis in a healthy patient.

Optionally, the expandable prosthesis is sponge-like. Optionally, the expandable prosthesis is inflatable. In some exemplary embodiments of the invention, the expandable prosthesis is adapted to be inserted between the tendons of the rotator cuff and the acromion and/or coracoid process. Expandable prosthesis is biocompatible and/or biodegradable, in an exemplary embodiment of the invention. Optionally, the expandable prosthesis is adapted to elute pharmaceutical agents once implanted in a patient's body. In an embodiment of the invention, inflatable expandable prosthesis is inflated with filler, for example a gas, liquid, and/or gel. Optionally, the filler is biocompatible and/or biodegradable. and/or contains the pharmaceutical agents. In some embodiments, elution of pharmaceutical agents is according to a schedule timed with the biodegradable properties of the expandable prosthesis. In some embodiments of the invention, the prosthesis is only partially filled.

In some embodiments of the invention, the prosthesis is provided with anchoring devices adapted to maintain the prosthesis in a steady relationship with the anatomical features around the implantation site. Optionally, the prosthesis is contoured along its exterior to accommodate anatomical features around the implantation site.

An aspect of some embodiments of the invention relates to a method for implanting an expandable prosthesis adapted to reduce and/or eliminate injury between soft tissues of the body and other tissues, for example to the rotator cuff. In an embodiment of the invention, the expandable prosthesis is either sponge-like or inflatable and is expanded in a space between the tendons of the rotator cuff and the acromion and/or coracoid process. In some embodiments of the invention, a prosthesis implantation and/or inflation device is used to implant and/or inflate the expandable prosthesis.

An aspect of some embodiments of the invention relates to an expandable prosthesis for treating inflammation and/or infection. Optionally, the expandable prosthesis is a sponge-like structure, sponge-like being defined as including at least one of the following properties: porous, absorbent and/or compressible. Optionally, the expandable prosthesis is inflatable. Expandable prosthesis is biocompatible and/or biodegradable, in an exemplary embodiment of the invention. Optionally, the expandable prosthesis is adapted to elute pharmaceutical agents once implanted in a patient's body. Expandable sponge-like device optionally contains within its cavities at least one biocompatible and/or biodegradable gelling material that expands when it comes into contact with at least one bodily fluid, for example by absorbing water.

In an embodiment of the invention, inflatable expandable prosthesis is inflated with filler, for example a gas, liquid, and/or gel. Optionally, the filler is biocompatible and/or biodegradable and/or contains the pharmaceutical agents. In some embodiments, elution of pharmaceutical agents is according to a schedule timed with the biodegradable properties of the expandable prosthesis.

In an embodiment of the invention, at least one section of the prosthesis is inflated with filler, for example a gas, liquid, cement and/or gel. Optionally, the filler is biocompatible and/or biodegradable. In some embodiments of the invention, the expandable prosthesis is adapted to have at least one section removed prior to closing the patient. In an embodiment of the invention, at least one section is adapted to withstand the expected pressures. In an embodiment of the invention, the expandable prosthesis is inflated and/or implanted using a plurality of prosthesis inflation and/or implantation devices.

An aspect of some embodiments of the invention relates to a prosthesis implantation and/or inflation device. In an embodiment of the invention, the prosthesis implantation and/or inflation device includes a syringe designed to inject filler into an expandable prosthesis, for example through a tube which operatively connects syringe to the expandable prosthesis. In some embodiments of the invention, the syringe is comprised of at least a plunger and a canister. Optionally, the plunger is advanced through the canister by the device in order to inject filler into the prosthesis. Optionally, the canister is advanced against the plunger, which remains relatively fixed due to counterforce from a backstop, in order to inject filler into the prosthesis.

In some exemplary embodiments of the invention, the prosthesis implantation and/or inflation device includes a safety. Optionally, the safety comprises at least a spring and a ball, wherein the ball acts as a counterpart to a groove in the backstop. Excessive force on the backstop by continued advancement of the canister towards the plunger triggers the safety, popping the ball out of the groove and freeing the backstop to move. In an embodiment of the invention, the placement of the backstop is according to a predetermined level of desired inflation of the prosthesis.

There is thus provided in accordance with an embodiment of the invention, a prosthesis comprising: a member designed to simulate at least one of a size or a shape of a naturally occurring bursa.

In an embodiment of the invention, the member is expandable. Optionally, the member is designed to be at least partially inflated. Optionally, the member is inflated sufficiently to reduce rubbing of the soft tissues against other tissues while permitting at least some movement of the soft tissues relative to the other tissues. Optionally, at least some movement of the soft tissues relative to the other tissues is full movement. In an embodiment of the invention, the member is sponge-like. Optionally, the sponge-like member is provided with a fluid absorbent material which when fluids are absorbed induces expansion of the sponge-like expandable member.

In an embodiment of the invention, the prosthesis is constructed of at least one of a biocompatible or biodegradable material. Optionally, the at least one of a biocompatible or biodegradable material is poly(lactice acid-co-epsilon caprolactone), PCL, PGA, PHB, plastarch material, PEEK, zein, PLA, PDO, PLGA, collagen or methyl cellulose.

In an embodiment of the invention, the prosthesis is constructed of at least one non-biodegradable material. Optionally, the at least one non-biodegradable material is polyethylene, polyurethane, silicon, or poly-paraphenylene terephthalamide.

In an embodiment of the invention, the prosthesis further comprises a rigid ring having a lumen therein attached to the member, wherein the lumen provides fluid communication to an inner space of the member.

In an embodiment of the invention, the prosthesis further comprises a plug designed to lodge in the lumen thereby sealing the inner space of the member. Optionally, the plug is constructed of at least one of a biocompatible or biodegradable material.

In an embodiment of the invention, the member is elastic.

In an embodiment of the invention, the prosthesis further comprises at least one anchoring device for stabilizing the prosthesis upon implantation. Optionally, the at least one anchoring device is constructed of at least one of a biocompatible or biodegradable material.

In an embodiment of the invention, the member is contoured to act as a counterpart to natural anatomical features of an implantation site.

In an embodiment of the invention, the member is designed to elute at least one pharmaceutical agent.

In an embodiment of the invention, the size of the prosthesis is approximately 2 cm to 15 cm in length, optionally 10 cm or less, along a long axis, approximately 2 cm to 10 cm in length, optionally 7 cm or less, along a short axis and approximately 0.5 mm to 20 mm in height, when expanded.

In an embodiment of the invention, the member is rigid. Optionally, the member is contoured to act as a counterpart to natural anatomical features of an implantation site while permitting at least some movement of the soft tissues relative to other tissues.

In an embodiment of the invention, the member is designed for use in a rotator cuff. In an embodiment of the invention, the member is designed for use in at least one of a flexor or an extensor. In an embodiment of the invention, the member is designed for use between a quadriceps and a femur. In an embodiment of the invention, the member is designed for use between a skin and a plantar fascia and a calcaneus of the body. In an embodiment of the invention, injury is at least one of inflammation or infection.

There is further provided in accordance with an exemplary embodiment of the invention, a method for implanting a prosthesis between soft tissues and other tissues of a body, comprising: placing the prosthesis into an implantation site between the soft tissues and the other tissues; and, simulating with the prosthesis a bursa naturally occurring at the implantation site. In an embodiment of the invention, the method further comprises eluting at least one pharmaceutical agent from the prosthesis at the implantation site. Optionally, placing and simulating occurs without significantly reducing movement of the soft tissues relative to the other tissues. Optionally, the soft tissues are tendons of a rotator cuff and the other tissues are at least one of a humerus, an acromion or a coracoid process.

There is further provided in accordance with an exemplary embodiment of the invention, a system for sealing an inflatable prosthesis, comprising: a prosthesis inflation device; a tube operatively connected to the prosthesis near one end and the prosthesis inflation device on the other end; a plug attached to the tube at the prosthesis end of the tube; and, a rigid ring attached to the prosthesis and slidably attached around the tube between the prosthesis inflation device and the plug; wherein pulling the tube towards the prosthesis inflation device causes plug to lodge in the rigid ring, sealing the prosthesis with the plug. Optionally, the plug is attached to the tube by gripping protrusions.

There is further provided in accordance with an exemplary embodiment of the invention, a method of sealing an inflatable prosthesis, comprising: pulling a tube out of the prosthesis and through a rigid ring; and, lodging a plug located on the end of the tube in the rigid ring.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIGS. 7A-B are flowcharts demonstrating methods of implanting an expandable prosthesis, in accordance with some exemplary embodiments of the invention;

DETAILED DESCRIPTION OF EXEMPLARY EMBODIMENTS

Figure 1:
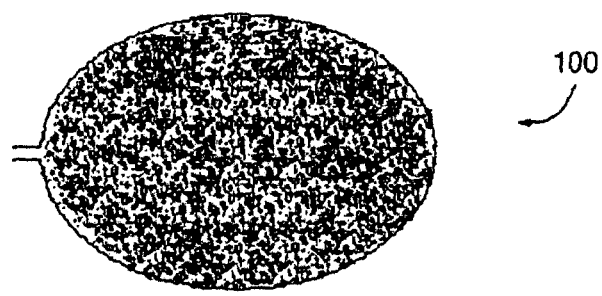
FIG. 1 is an illustration of a sponge-like expandable prosthesis in accordance with an exemplary embodiment of the invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "In some embodiments" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As described above, repeated strenuous motion often causes sensitive soft tissues associated with a mammalian joint to suffer wear and tear injuries from repeatedly rubbing against one another and/or hard tissues, such as bone. Tears of tendons and/or ligaments and articular capsule disintegration are examples of this type of injury. In addition, these tissues can be adversely affected by inflammation, infection, disease and/or genetic predispositions which lead to degeneration of these tissues.

Injuries to soft tissues such as tendons can cause pain and impaired function of the area served by the tendon. Typically, a bursa can be found near areas where "friction" injuries due to the rubbing are prone to occur. A bursa is a natural fluid collection that permits movements between tendons and/or ligaments and bone parts and prevents injury to these tendons by acting as a cushion and/or movement facilitator between them.

In some embodiments of the invention, prostheses described herein are shaped and/or sized to simulate the natural bursa found in the intended area of implantation. For example, in some of the rotator cuff embodiments described below, the described exemplary prostheses are shaped and/or sized to simulate the subacromial bursa. Optionally, in some embodiments, the prostheses are sized to supplement a natural bursa which is misshapen and/or undersized, bringing the combination of the natural bursa and the prosthesis into line with the shape and/or size of a healthy bursa.

In some embodiments of the invention, prostheses described herein possess viscoelastic deforming characteristics in the sense that they combine plastic as well as elastic characteristics. In some embodiments, the prostheses described herein are designed and configured to gently resist an immersion of a bony prominence and to slowly regain at least partially an expanded size once normal stresses diminishes.

In some embodiments of the invention, prostheses described herein include an inflatable chamber (e.g., a bladder) having at least one malleable wall, optionally elastic or semi-elastic, optionally made from a non-compliant or a semi-compliant material, provided in contact with a bony prominence under dynamic and continuously changing pressures and immersion capacities. In some embodiments, the wall is subjected to deform by at least partially imprinting immersions, optionally its deforming does not result in a substantial increase in stress therein. In some embodiments, the malleable wall is supported with a fluid, either Newtonian or non-Newtonian, which fills the chamber to a less than a maximal inflation volume and therefore allowed to freely flow and redistribute under continuously changing chamber form and/or volume. In some embodiments, the chamber is filled to a certain chosen degree in order that the chamber will avoid bottoming under maximally known compressive forces, in the sense that any opposing surfaces thereof will not engage. In some embodiments, a chosen filling volume is patient-specific, optionally determined according to a maximally allowed elevated in-chamber pressure at a maximally known compressive force. In some embodiments, the chamber includes at least two opposing walls in continuous contact with two opposing body prominences of a mammalian joint/articulation. In some embodiments, the walls are nonstrechable in transverse plane of the prosthesis under normal sear forces created in the articulation but is pliable other planes. In some embodiments, the at least one wall or at least two walls are peripherally and/or laterally supported with a stiffer portion of the chamber, acting as a frame support.

In some embodiments of the invention, the described exemplary prostheses are implanted in a collapsed form thereby allowing minimally invasive related techniques and instrumentation. In some embodiments, such implantation may include a delivery to site via a small incision and/or created passage having a maximally preferred size (e.g., diameter) equal or less than 5 mm, optionally equal or less than 3 mm.

In some embodiments, the described exemplary prostheses are expanded in site to a first form and/or size, thereby irreversibly uncollapsible.

In some embodiments, the described exemplary prostheses are expanded and/or contracted from the first form and/or size to a second form and/or size, thereby achieving a chosen dimension, characteristic and/or functionality derived from the prostheses form and/or size.

In some embodiments, the described exemplary prostheses are regulated such to contract down to a patient-specific and/or a minimal value and/or to build a maximally allowed inner pressure, thereby to provide a chosen prosthesis consistency (e.g., a maximal malleability) but still maintain a minimally allowed distance and/or avoiding any physical contact between adjacent tissues (e.g., adjacent joint bones) under any non-breaking compressive stresses applied to the implanted prosthesis: In some embodiments, the pressure regulated expandable prostheses of the present invention are singularly programmed or calibrated to a patient, in-vivo, to thereby set a maximally allowed generated pressure to a maximal prosthesis contraction under a certain movement scenario of a hosting environment (e.g., the host shoulder).

In some embodiments, the present invention relates to joints including, but not limited to shoulder joints and bodily areas adjacent joints and/or interlinked with joints' function, such as the rotator cuff. The rotator cuff is an anatomical term given to the group of muscles and their tendons that act to stabilize the shoulder and to permit rotation and abduction of the arm. Along with the teres major and the deltoid, the four muscles of the rotator cuff make up the six muscles of the human body which connect to the humerus and scapula. Injury to the tendons and/or these muscles can cause pain and impaired function of the shoulder. The subacromial bursa is a natural fluid collection that permits movement of these rotator cuff tendons beneath the acromion and coracoid process, both of which are part of scapula bone. In some rotator cuff injuries, the subacromial bursa becomes inflamed and suffers from a reduced ability to prevent injury to the tendons through friction.

Referring to FIG. 1, an expandable prosthesis 100 is shown as an exemplary embodiment of the invention. In an exemplary embodiment of the invention, expandable prosthesis 100 is introduced between the above mentioned acromion and coracoid processes and the rotator cuff tendons and designed to permit relatively unhindered (relative to the movement afforded to the shoulder without treatment) or free shoulder movement, shown and described in more detail with respect to FIG. 3. In some embodiments of the invention, expandable prosthesis 100 comprises an expandable member which is a sponge-like structure. In some embodiments, the sponge-like expandable prosthesis 100 is adapted to elute pharmacological substances such as anti-inflammatory and/or antibiotic and/or pro-angiogenesis substances, in some exemplary embodiments of the invention.

In an exemplary embodiment of the invention, the expandable prosthesis 100 is biodegradable and/or biocompatible. In some embodiments, the sponge-like structure is manufactured from at least one biodegradable and/or biocompatible synthetic material such as, but not limited to, polycaprolactone ("PCL"), polyglycolide ("PGA"), polyhydroxybutyrate ("PHB"), plastarch material, polyetheretherketone ("PEEK"), zein, polylactic acid ("PLA"), polydioxanone ("PDO"), poly(lactic-co-glycolic acid) ("PLGA"), poly(lactice acid-co-epsilon caprolactone) or any combination and/or family members thereof. In some exemplary embodiments of the invention, the sponge-like structure is manufactured from at least one "naturally-derived" biodegradable and/or biocompatible materials such as collagen and/or methyl cellulose. In an exemplary embodiment of the invention, sponge-like expandable prosthesis 100 is imparted expandable properties, at least in part, by placing within its cavities at least one biocompatible and/or biodegradable material which expands after coming into contact with fluids. Optionally, in some embodiments, the fluids are bodily fluids. Optionally, in some embodiments, the at least one biocompatible and/or biodegradable material is a gel.

In some embodiments, the implant can be used to prevent pain and/or friction for a predetermined duration during which there is at least partial self-healing of adjacent tissues. In some embodiments, the implant can be used until it is punctured and/or degraded.

In some exemplary embodiments of the invention, sponge-like expandable prosthesis 100 is non-biodegradable. Non-biodegradable expandable prostheses are manufactured of biocompatible materials such as polyethylene, Kevlar® (poly-paraphenylene terephthalamide), polyurethane or silicon, or any combination thereof, in some embodiments of the invention. In some exemplary embodiments of the invention, the expandable prosthesis is manufactured from biologically derived, biocompatible and/or biodegradable materials such as collagen. In an exemplary embodiment of the invention, prosthesis 100, when expanded, has approximately the same dimensions as other prostheses when expanded, described below.

Figure 2:
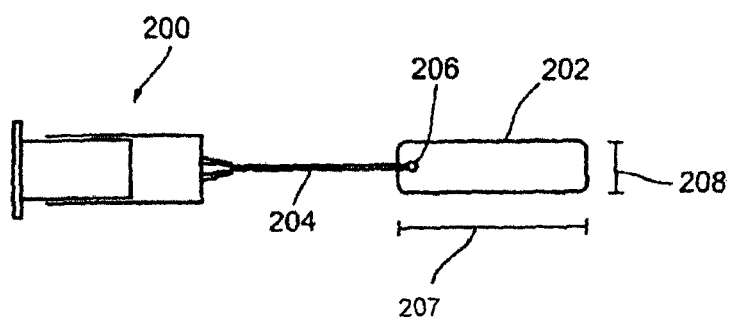
FIG. 2 is a cutaway view of a portion of a prosthesis implantation and/or inflation device and an inflatable expandable prosthesis, in accordance with an exemplary embodiment of the invention.

Referring to FIG. 2, a cutaway view of a portion of a prosthesis implantation and/or inflation device 200 and a prosthesis 202 with an expandable member which is inflatable is shown, in accordance with an exemplary embodiment of the invention. In an exemplary embodiment of the invention, inflatable expandable prosthesis 202 is introduced between the acromion and coracoid processes and the rotator cuff tendons designed to permit relatively unhindered or free shoulder movement, shown and described in more detail with respect to FIG. 3. Optionally, in some embodiments, alternatively and/or additionally, an expandable prosthesis comprises an inflatable structure and a sponge-like structure in combination.

In an exemplary embodiment of the invention, inflatable expandable prosthesis 202 is rectangular shaped when deflated and resembles a cuboid parallelepiped when inflated. In an exemplary embodiment of the invention, inflatable expandable prosthesis 202 is circular or oval in shape when deflated and when inflated resembles a cylindrical disc or ovoid. In some embodiments, many shapes could be adapted to be implanted between the acromion and coracoid processes and the rotator cuff tendons designed to permit relatively unhindered or free shoulder movement for a patient, in an exemplary embodiment of the invention. In some embodiments of the invention, prosthesis 202 is adapted to be inserted deflated into a patient's body through a cannula. Optionally, in some embodiments, the cannula is a 5 mm-7 mm cannula. In an embodiment of the invention, a long axis 207 (x-axis) of inflatable expandable prosthesis 202 is approximately 2 cm to 10 cm in length when inflated. In some embodiments of the invention, a short axis 208 (y-axis) of inflatable expandable prosthesis 202 is approximately 2 cm to 10 cm in length when inflated. In some exemplary embodiments of the invention, inflatable expandable prosthesis 202 is 0.5 mm to 20 mm in height (z-axis). Optionally, in some embodiments, inflatable expandable prosthesis 202 is 1 mm to 10 mm in height. In some embodiments, the deflated and/or inflated size of prosthesis 202 may be adapted to fit for a patient's particular needs or to simulate the size and/or shape of the natural bursa, in an embodiment of the invention, and therefore, prosthesis 202 does not necessarily conform to the size ranges given above.

In some embodiments, inflatable expandable prosthesis 202 is manufactured by dip molding, in an exemplary embodiment of the invention. In some embodiments of the invention, inflatable expandable prosthesis 202 is a seamless balloon-like structure made from biocompatible and/or biodegradable synthetic materials such as, but not limited to; PCL, PGA, PHB, plastarch material, PEEK, zein, PLA, PDO, PLGA, poly(lactice acid-co-epsilon caprolactone) or any combination and/or family members thereof. Additionally, optionally and/or alternatively, in some embodiments, inflatable expandable prosthesis 202 is manufactured from natural, biocompatible and/or biodegradable materials such as collagen and/or methyl cellulose. In some exemplary embodiments of the invention, the inflatable prosthesis 202 is manufactured from at least one non-biodegradable material such polyethylene, polyurethane, silicon, and/or Kevlar®. In an embodiment of the invention, prosthesis 202 is comprised of a material which is approximately 100-200 microns in thickness, although, as with the other dimensions, the thickness dimension of the material is adapted depending on the intended use and/or the needs of the patient. In some exemplary embodiments of the invention, inflatable expandable prosthesis 202 is adapted to elute pharmaceuticals such as anti-inflammatory drugs and/or antibiotics and/or pro-angiogenesis factors to promote healing.

Inflatable expandable prosthesis 202 is releasably attached to prosthesis implantation and/or inflation device 200, in an exemplary embodiment of the invention. Prosthesis implantation and/or inflation device 200 is adapted to inflate and/or deflate prosthesis 202, allow prosthesis 202 to be positioned in vivo, and/or separate from prosthesis 202 after implantation, leaving prosthesis 202 at the implantation site, in an embodiment of the invention. In some exemplary embodiments of the invention, prosthesis implantation and/or inflation device 200 includes a tube or catheter type structure 204 which interfaces with prosthesis 202 in the proximity of a sealing mechanism 206 which is located at the end of tube 204 nearest prosthesis 202.

Figure 4A:
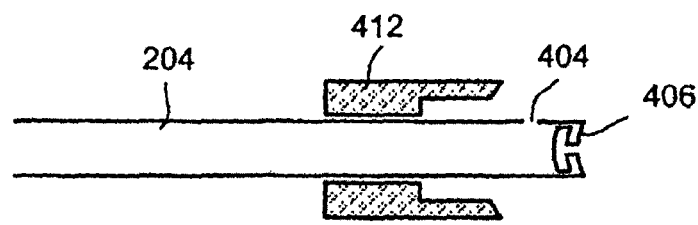
FIGS. 4A-C are cutaway side views showing the progression removably attaching a prosthesis implantation and/or inflation device and an expandable prosthesis, in accordance with an exemplary embodiment of the invention.
Figure 4B:
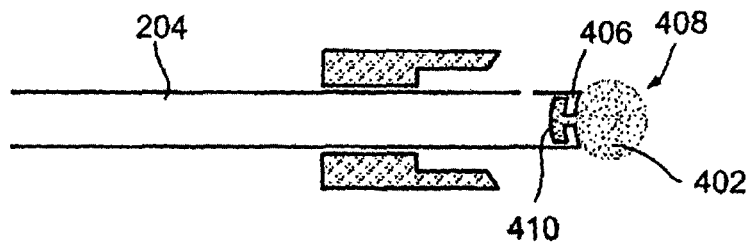

In an embodiment of the invention, sealing mechanism 206 includes a plug 402, shown in FIG. 4B inter alia, attached to the end of tube 204 nearest prosthesis 202. In an embodiment of the invention, plug 402 is constructed of the same material or materials as any of the prostheses described herein. In some embodiments, tube 204 is adapted to allow passage therethrough of a filler to inflate prosthesis 202, for example by placing at least one orifice 404 in tube 204. In some embodiments of the invention, the filler is air. Additionally, alternatively and/or optionally, in some embodiments, the filler is a biodegradable and/or biocompatible material and/or fluid. In some embodiments, the biodegradable material and/or fluid is saline. In some embodiments of the invention, the filler is a gel and/or liquid. In an embodiment of the invention, tube 204 is provided with gripping protrusions 406 in order to increase the contact surface between tube 204 and plug 402 and therefore the force that may be applied to plug 402 when sealing prosthesis 202. In some embodiments of the invention, plug 402 is ovoid shaped, and/or has a shape such that plug's 402 loose end 408 is larger than the attached end 410 so that, as described in more detail below with respect to FIGS. 4A-C, 5 and 7, plug 402 seals inflatable expandable prosthesis 202 during implantation.

Figure 4C:
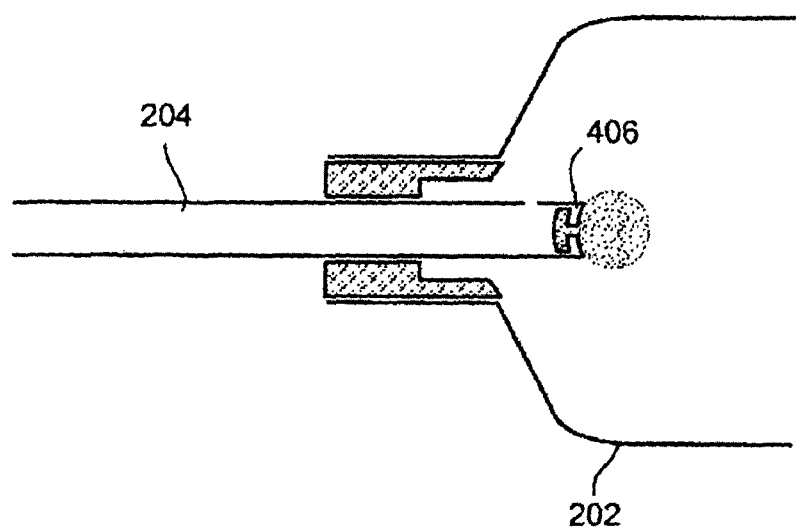

FIGS. 4A-C are cutaway side views showing the progression of removably attaching prosthesis implantation and/or inflation device 200 and prosthesis 202, in accordance with an exemplary embodiment of the invention. Referring to FIG. 4A, in some embodiments, a rigid ring 412 is cast on and/or connected to tube 204 of prosthesis implantation and/or inflation device 200, in an embodiment of the invention. In an embodiment of the invention, rigid ring 412 fits snugly onto tube 204 such that air and/or other fluid injected into prosthesis 202 does not escape via the intersection of rigid ring 412 and tube 204, however tube 204 is slidable in relation to rigid ring 412. This slidability is used, for example, when prosthesis implantation and/or inflation device 200 is separated from prosthesis 202 in accordance with an exemplary embodiment of the invention. In an exemplary embodiment of the invention, plug 402 is cast on tube 204 such that gripping protrusions 406 grasp at least a portion of attached end 410 of plug 402, shown in FIG. 4B. Optionally, mold injection and/or dip molding, and/or any other method known in the art, may be used for manufacturing plug. At least tube 204 and/or plug 402 and/or rigid ring 412 are made of biodegradable and/or biocompatible materials, in an embodiment of the invention.

In some embodiments, rigid ring 412 is cast on or connected to tube 204 before plug 402 is cast tube 204 because in an exemplary embodiment of the invention, plug 402 has a larger diameter than the inner diameter of rigid ring 412 thereby preventing plug 402 from passing through rigid ring 412. In an embodiment of the invention, inflatable expandable prosthesis 202 is placed around plug 402 and tube 204 such that tube 204 and plug 402 extend into a cavity proscribed by prosthesis 202. Prosthesis 202 is attached to an exterior surface of rigid ring 412 such that air and/or other fluid injected into prosthesis 202 does not escape via the intersection of prosthesis 202 and rigid ring 412, in an embodiment of the invention. Optionally, a thermal and/or chemical method is used to attach prosthesis 202 to rigid ring 412.

Figure 5:
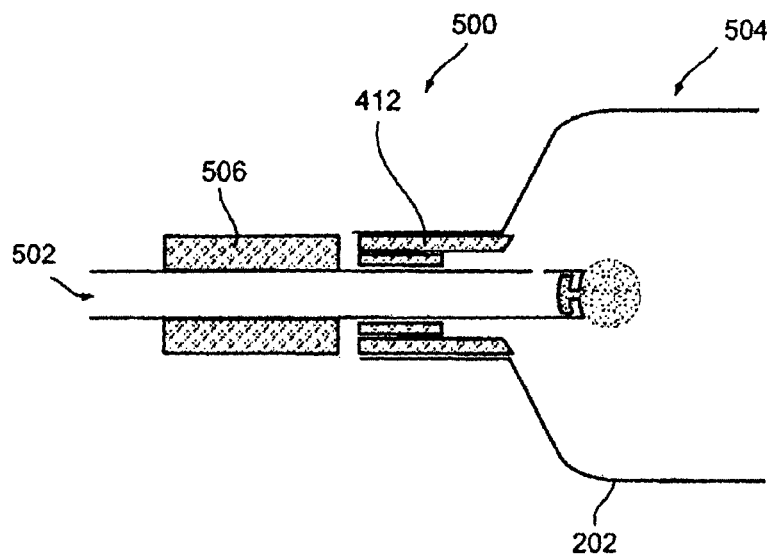
FIG. 5 is a cutaway side view of a portion of a prosthesis implantation and/or inflation device including a counter-pressure sheath and an expandable prosthesis, in accordance with an exemplary embodiment of the invention.

FIG. 5 shows an assembly 500 including a portion 502 of inflation device 200 and a portion 504 of expandable prosthesis 202 further comprising a counterforce ring 506, in accordance with an exemplary embodiment of the invention. In an embodiment of the invention, counterforce ring 506 is adapted to apply counterforce to rigid ring 412 during separation of prosthesis inflation device 200 from prosthesis 202, as described in more detail below with respect to FIG. 7. In some embodiments of the invention, counterforce ring 506 is constructed of a biocompatible material, for example stainless steel and/or plastic, that is approximately at least as hard as rigid ring 412.

Figure 6:
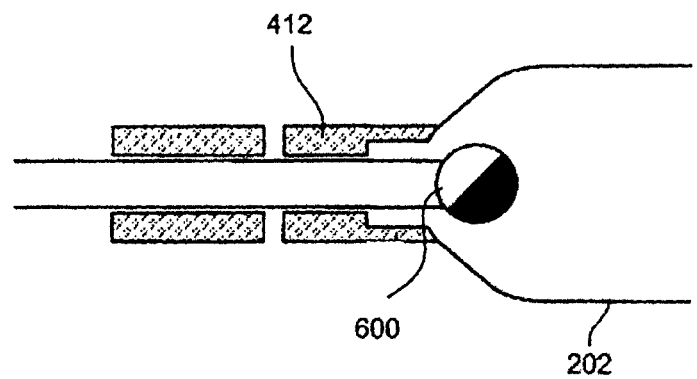
FIG. 6 is a cutaway side view of an alternative sealing mechanism, in accordance with an exemplary embodiment of the invention.

In some embodiments of the invention, at least one pressure regulating valve 600, shown in FIG. 6, is used in addition to or alternatively to plug 402 and rigid ring 412 for sealing prosthesis 202 after at least partially inflating prosthesis 202 with prosthesis implantation and/or inflation device 200. In some embodiments, pressure regulating valve 600 allows only addition of the filler. In some embodiments, pressure regulating valve 600 allows release of filler based on a predetermined and/or pre-set pressure in the prosthesis 202. In some embodiments, pressure regulating valve 600 allows unhindered inflation but allows deflation based on a predetermined pressure inside prosthesis 202. In some embodiments, the maximal inflation volume is between 5 to 100 cubic centimeters (cc), optionally 10 to 60 cc, optionally 15 to 45 cc, or higher, or lower, or intermediate. In some embodiments, the final (partially inflated) volume is between 0.5 to 60 cc, optionally 5 to 40 cc, optionally 9 to 30 cc, or higher, or lower or intermediate. In some embodiments, inflating the implant by adding a first amount of filler causes the implant to fully expand, fully unroll, and/or expand a void to a predetermined shape and/or size.

In some embodiments, pressure regulating valve 600 is deployed for effective operability at a certain/chosen interval during implantation, deploying and/or setting up of prosthesis 202 at the hosting environment. In some embodiments, pressure regulating valve 600 is set to operate after inflating prosthesis 202 to a maximal or otherwise chosen value. In some embodiments, pressure regulating valve 600 allows filler to be released out until pressure in prosthesis 202 goes down to a chosen value, e.g., a maximally allowed pressure. In some embodiments, the pressure regulating valve 600 allows filler to be released into a void space in the joint. This is achievable, for example, if pressure regulating valve 600 is set to burst over a threshold value which may be same or slightly greater or smaller than the maximally allowed pressure. Certain external forces may be applied, either passively by a physician and/or actively by the patient, for example forces exerted by maneuvering the hosting environment (e.g., the joint or an adjoined arm), to thereby expel out from prosthesis 202. After utilizing pressure regulating valve 600, in some embodiments, it may then be neutralized or discarded and/or prosthesis 202 may be sealed.

In some embodiments, the pressure regulating valve 600 is attached to the prosthesis. In some embodiments, the pressure regulating valve is external from the implant. In some embodiments, the pressure regulating valve 600 is biodegradable and/or biocompatible. In some embodiments, the valve 600 is manufactured from at least one biodegradable and/or biocompatible synthetic material such as, but not limited to, polycaprolactone ("PCL"), polyglycolide ("PGA"), polyhydroxybutyrate ("PHB"), plastarch material, polyetheretherketone ("PEEK"), zein, polylactic acid ("PLA"), polydioxanone ("PDO"), poly(lactic-co-glycolic acid) ("PLGA"), poly(lactice acid-co-epsilon caprolactone) or any combination and/or family members thereof. In some exemplary embodiments of the invention, the valve is manufactured from at least one "naturally-derived" biodegradable and/or biocompatible materials such as collagen and/or methyl cellulose.

In some exemplary embodiments of the invention, valve 600 is non-biodegradable. Non-biodegradable valves 600 are manufactured of biocompatible materials such as polyethylene, Kevlar® (poly-paraphenylene terephthalamide), polyurethane or silicon, or any combination thereof, in some embodiments of the invention. In some exemplary embodiments of the invention, the valve 600 is manufactured from biologically derived, biocompatible and/or biodegradable materials such as collagen.

Figure 3:
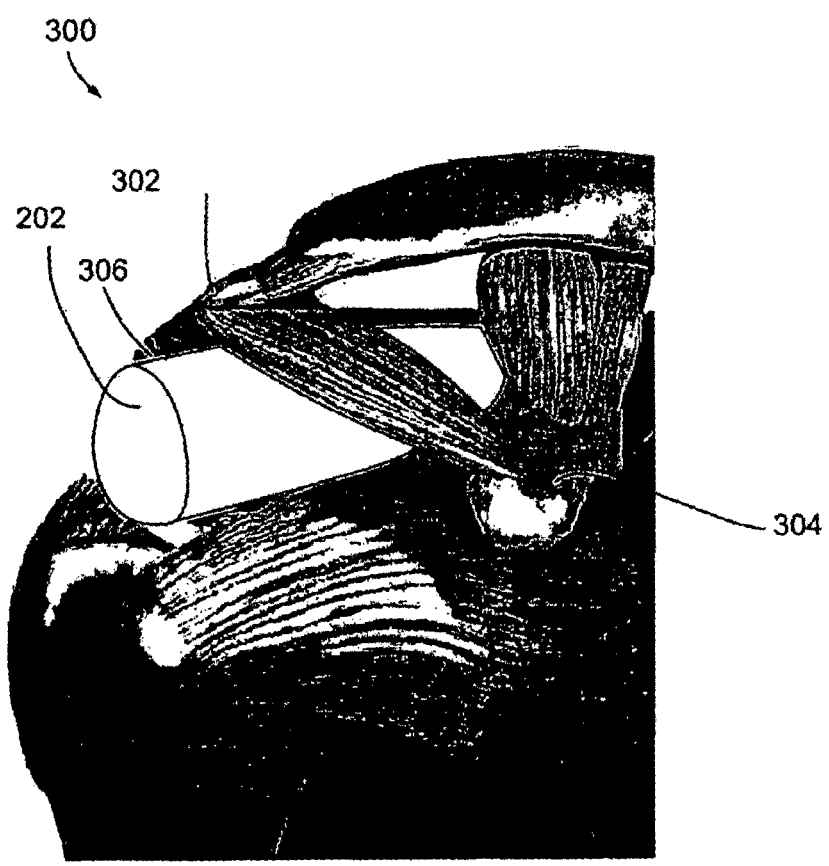
FIG. 3 is an anatomical view of a human shoulder with an expandable prosthesis in vivo, in accordance with an exemplary embodiment of the invention.

FIG. 3 shows an anatomical view of a human shoulder 300 with an expandable prosthesis 100, 202 in vivo, in accordance with an exemplary embodiment of the invention. Prosthesis 100, 202 is inserted between the acromion 302 and the coracoid process 304, in an embodiment of the invention. In some embodiments of the invention, prosthesis 100, 202 and any other prosthesis described herein, is inserted proximal to the bursa 306. Optionally, if there is no bursa 306 of any remarkable size, the prosthesis is inserted in lieu of bursa 306. In an embodiment of the invention, an implanted prosthesis, such as those described herein, is adapted to cover the humerus head during shoulder 300 motion, while remaining relatively fixed in relation to the acromion 302 and/or the coracoid process 304.

In some embodiments of the invention, an anchoring expandable prosthesis is adapted to prevent and/or reduce injury to the rotator cuff and/or to permit relatively unhindered or free shoulder movement, for example if the rotator cuff soft tissues are partially or completely torn and/or deteriorated. In some embodiments, the anchoring expandable prosthesis comprises an expandable member and at least one anchoring device which is adapted to be attached to a part of the patient, for example the humerus head/tendons, acromion and/or coracoid process, thereby anchoring the prosthesis in place. In an embodiment of the invention, the anchoring expandable prosthesis comprises at least one anchoring device attached to an expandable portion adapted to operate similarly to prostheses 100, 202. The at least one anchoring device is manufactured of biocompatible and/or biodegradable or non-biodegradable metals and/or alloys and/or composites, for example titanium, stainless steel or magnesium alloys. In an embodiment of the invention, the expandable portion is manufactured of biocompatible and/or biodegradable or non-biodegradable materials such as high density polyethylene or those described with respect to prostheses 100, 202. In an embodiment of the invention, the at least one anchoring device is attached to the expandable member using filaments and/or wires.

In some embodiments of the invention, prostheses described herein are adapted for anchoring, for example by contouring the outer surface such that surrounding tissues can be placed within the contours, thereby "anchoring" the device. In some embodiments of the invention, the contours are adapted to act as counterparts to anatomical features at the implantation site, whereby the features settle into the contours upon implantation, but still permit relatively unhindered movement of the treated area.

Alternatively, in some embodiments, the prostheses 100, 202 do not include anchoring and kept in place and/or be allowed to partial and/or limited relative movement with a tissue in contact due to shape correlation in the void maintained by peripheries of adjacent tissues. In some embodiments, prostheses 100, 202 are adapted for moving in a limited range of motion, optionally reflecting changes in surrounding boundaries due to joint movement. Such movements may alternatively or additionally derive from shifting between static to kinetic dry friction forces created between a surface of a prosthesis in contact with a moving tissue. In some embodiments, the prosthesis is selectively changed to impose a chosen maximal friction characteristic (e.g., a maximally allowed static friction force between a surface and a specific tissue type in contact), for example a friction coefficient and/or a normal force applied to the tissue in contact.

In some embodiments, prostheses 100, 202 are shaped, internally pressurized and/or inflated/deflated to a degree which maintains or facilitates, optionally in an allowed range of motion, a stable equilibrium in which the prosthesis will restore a nominal position when the joint returns to a non- or a less-stressed position and/or when the void substantially returns to a nominal shape and/or size, such as a shape and/or size during prosthesis implantation. Alternatively or additionally, prostheses 100, 202 are shaped, internally pressurized and/or inflated/deflated to a maximal predetermined or patient-specific size (e.g., a height), optionally while substantially not changing other dimensions (e.g., width and/or thickness), thereby avoiding potential dislocations due to tissue (e.g., bonny tissues) movements in the void. For example, an acromion portion may enter and/or decrease the height of the void (in this example: the subacromial space or portion thereof) during a shoulder movement (e.g., flexion and/or extension/external rotation) so if the prosthesis is inflated to a height greater than the void's decreased height, it may be forced by the acromion portion to dislocate; optionally out of the allowed range of motion and/or to an unstable equilibrium in an embodiment of the invention.

As mentioned above, prostheses 100, 202, and/or any of the other prostheses described herein, may be designed for use in places where there is sliding of soft tissues or other tissues, such as tendons against other tissues, such as bones as: a) between the quadriceps and femur after operations on the knee, b) near the finger flexor and/or extensor to prevent adhesions, for treatment of ailments such as carpal tunnel syndrome and/or, c) between the skin and plantar fascia and calcaneus in case of calcaneal spur, in some exemplary embodiments of the invention. As described above, the prosthesis used for treatment of particular ailments is sized and/or shaped to simulate the natural bursa found at the location being treated, in an exemplary embodiment of the invention. In some embodiments, same or different sliding characteristics facilitated by the prostheses of the present invention allow relative motion between hard tissue types, such as cartilages and/or bones, for example when tendons and ligaments are completely torn.

In an embodiment of the invention, an expandable prosthesis which is at least slightly elastic, but not inflatable, is designed to permit relatively unhindered or free shoulder movement. In some embodiments of the invention, the elastic prosthesis is manufactured from polyethylene and/or silicon and/or in combination with metals, such as titanium. Optionally, the elastic prosthesis is contoured to serve as a counterpart to the surfaces with which it will come into contact. For example in the case of a rotator cuff, the elastic prosthesis may be contoured to fit at least the acromion.

In an embodiment of the invention, a prosthesis is provided which is substantially rigid. The rigid prosthesis is constructed of a biocompatible material, for example stainless steel and/or a hard plastic, in some embodiments of the invention. Optionally, in some embodiments, the rigid prosthesis is also biodegradable. In some embodiments of the invention, the rigid prosthesis is adapted to act as a counterpart to at least one anatomical feature at the implantation site, whereby the feature mates with the rigid prosthesis upon implantation, but still permits relatively unhindered movement of the treated area. As an example, the rigid prosthesis is adapted to mate with both the humerus head and the acromion upon implantation, in an embodiment of the invention.

Referring to FIG. 7A, a method 700 of implanting an expandable prosthesis 100, 202, or any other prosthesis described herein is described, in some exemplary embodiments of the invention. In an embodiment of the invention, implantation method 700 is adapted for implantation of prostheses 100, 202, or any other prosthesis described herein, into the shoulder of a patient to prevent and/or reduce injury to the rotator cuff and/or to permit relatively unhindered or free shoulder movement. In an embodiment of the invention, prostheses 100, 202, or any other prosthesis described herein, are introduced percutaneously or by making (702) a small incision, optionally performed by posterior, lateral or anterior approaches using, for example, palpation, arthroscopy, ultrasound ("US"), computed tomography ("CT"), magnetic resonance imaging ("MRI"), fluoroscopy, transmission scan ("TX"), or any combination thereof. In an embodiment of the invention, a needle is inserted (704) into the void space between the rotator cuff tendons and the acromion 302 and coracoid process 304. A guide wire is introduced (706) via the needle into the void space between the rotator cuff tendons and the acromion 302 and coracoid process 304, in an exemplary embodiment of the invention. In some embodiments of the invention, a dilator is placed (708) over the guide wire and extended into the space. Subsequently, a trocar of the dilator is removed (710), leaving a dilator sheath in place in some embodiments.

Figure 8:
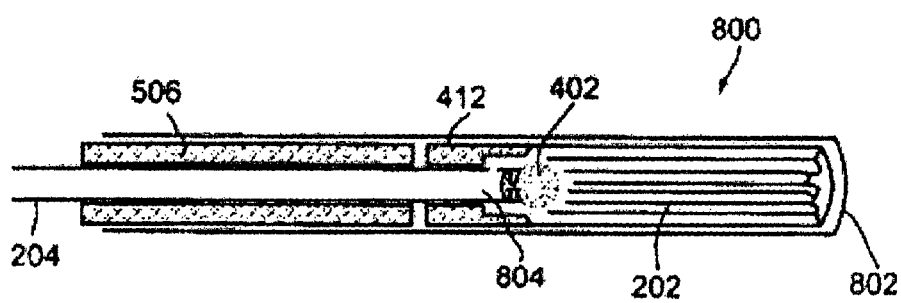
FIG. 8 is a cutaway side view of an expandable prosthesis packed prior to use, in accordance with an exemplary embodiment of the invention.

In an embodiment of the invention, inflatable expandable prosthesis 202 is placed (712) into the void space using the dilator sheath and/or the prosthesis inflation device 200 for guidance and/or movement impetus. Once prosthesis 202 is approximately in the proper position, in some embodiments, the dilator sheath and an external sheath 802 of prosthesis inflation device 200, shown and described in more detail with respect to FIG. 8, are withdrawn (714) to allow for inflation (716) of prosthesis 202. Inflation (716) using prosthesis inflation device 200 is described in more detail below. Inflation (716) of prosthesis 202 is achieved, in some embodiments of the invention, during arthroscopy. In some embodiments of the invention, for example if prosthesis 202 is implanted during open surgery or arthroscopy, proper deployment of prosthesis 202 is ascertained by visual inspection of prosthesis 202. In an embodiment using arthroscopy, prosthesis may be introduced through an arthroscopy port. In some embodiments of the invention, inflation (716) is achieved using palpation and US guidance to ascertain proper deployment of prosthesis 202. In some embodiments of the invention, inflation (716) is achieved using fluoroscopy to ascertain proper deployment of prosthesis 202. Proper deployment of prostheses, in some embodiments of the invention, means no interposition of tendons and/or other soft tissue between the implanted prosthesis and acromion 302 or coracoid process 304 and/or that during movement of the humerus, the prosthesis remains below acromion 302.

Inflation (716) of prosthesis 202 is performed using prosthesis inflation device 200, in an embodiment of the invention. Referring to FIG. 8, an expandable prosthesis 202 is shown packed for implantation and prior to deployment, in accordance with an exemplary embodiment of the invention. Components of the assembly 800 are enclosed in an external sheath 802 which surrounds at least prosthesis 202, in an exemplary embodiment of the invention. External sheath 802 is adapted to maintain prosthesis 202 in a collapsed condition during placing (712) in order to ease insertion of prosthesis 202 into the implantation space or site through the dilator sheath, in an embodiment of the invention. As described above, once prosthesis 202 is in the implantation space, external sheath 802 is removed, enabling prosthesis 202 to be inflated without hindrance apart from the body parts against which prosthesis 202 is pressing in an embodiment of the invention.

In an embodiment of the invention, inflation (716) of prosthesis 202 is performed by adding a sufficient filler such as physiologic fluid such as saline, Hartman or Ringer solutions and/or any other biocompatible and/or biodegradable fluid. In some embodiments of the invention, inflation (716) is performed using a biocompatible and/or biodegradable gel. In an embodiment of the invention, inflation (716) of prosthesis 202 is performed using a gas, for example air and/or carbon dioxide. In some embodiments of the invention, the inflating gel and/or fluid contains pharmaceutical agents, for example anti-inflammatory drugs and/or antibiotics and/or pro-angiogenesis factors to promote healing, which are eluted into the patient's body. In some embodiments of the invention, prosthesis 202 is inflated to the maximum volume possible without reducing the shoulder's range of movement. In an embodiment of the invention, prosthesis 202 is filled to less than its maximum volume in order to permit shifting of the contents of prosthesis 202 during movement. Optionally, in some embodiments, the prosthesis 202 is filled to 50%-70% of its maximal inflation volume (for example, an expandable member with a 14 cc volume is filled with 9 cc of filler). It should be noted that other prosthesis embodiments described herein are deployed in a similar fashion, in some embodiments of the invention.

Sealing (718) of prosthesis 202, once inflated to the desired level, is performed by pulling tube 204 towards rigid ring 412 as they slide in relation to one another plug 402 becomes lodged in a lumen 804 of rigid ring 412 and continued pulling brings rigid ring 412 into contact with counterforce ring 506, in an embodiment of the invention. In an embodiment of the invention, tube 204 passes through lumen 804 with lumen 804 providing fluid communication between prosthesis implantation and/or inflation device 200 and an inner space defined by the dimensions of prosthesis 202. In an embodiment of the invention, an attending medical professional performing the implantation procedure holds counterforce ring 506 substantially steady while pulling on tube 204 away from the patient. Optionally, in an embodiment, prosthesis inflation device 200 is adapted to perform the steadying of counterforce ring 506 and/or retraction of tube 204 automatically. In some embodiments of the invention, a mechanism is provided to prosthesis inflation device 200 which translates rotational movement to a retracting force on tube 204. Optionally, rotation movement is applied manually.

Continued pulling ("retraction" away from patient) of tube 204 causes a portion of plug 402 to break off, the portion of plug 402 lodging itself in lumen 804 of rigid ring 412 thereby sealing (718) prosthesis 202. In some embodiments of the invention, the portion of plug 402 becomes partially deformed as it lodges in lumen 804. Prosthesis inflation device 200 (referred to as "implantation device" in the figure), now being separated from prosthesis 202 as a result of sealing (718) is withdrawn (720) from the patient and patient is closed, in an exemplary embodiment of the invention. It should be understood that in some embodiments of the invention, a sponge-like expandable prosthesis device is used and therefore, inflation (716) and inflation related actions may not be carried out, for example prosthesis 100 expands rather than inflates.

In an exemplary embodiment of the invention, the implanted prosthesis is secured, using methods known in the art, to soft tissue and/or bone to prevent the prosthesis from being easily displaced by shoulder movement. In some embodiments of the invention, sutures, clips and/or anchors are used to secure the prosthesis in place. Optionally, an anchoring expandable prosthesis is used. In an embodiment of the invention, simulating a naturally occurring bursa using a prosthesis is an action taken with respect to method 700. Optionally, simulating is related to inflation (716) in that the prosthesis is inflated to resemble the appropriate size and/or shape and/or characteristics (malleability, compressibility, etc.) of the naturally occurring bursa. In an embodiment of the invention, placing the prosthesis at the implantation site and simulating a naturally occurring bursa does not significantly reduce movement of the soft tissues being protected in relation to the other tissues at the implantation site.

In an exemplary embodiment of the invention, prosthesis 100 is implanted by placing prosthesis 100 into a cannula, such as those described elsewhere herein, and advancing it to the implantation site using a plunger.

In an exemplary embodiment of the invention, prosthesis 100 or the elastic prosthesis, described above, is implanted by inserting the device directly through a small incision, without a cannula, near the implantation site.

FIG. 7B shows a method for implanting prostheses 100, 202, or any other prosthesis described herein according to another embodiment. In an embodiment, an incision is made (731) as known in the art and/or similar to step 702 above. Optionally, in some embodiments, a passage from incision and/or an implantation space are created (732). Passage and/or implantation space may be created (732) manually/digitally and/or by using a dedicated instrument, such as a dilator in some embodiments. Alternatively, a passage and/or an implantation space are anatomically and/or readily present in some embodiments. Alternatively or additionally, a passage to an anatomical space (e.g., a subacromial space) is created (732) by pushing therethrough the prosthesis and/or any implantation/delivery apparatus in some embodiments. Once the implantation site is located and/or prepared, as discussed above, a sized prosthesis, such as any of prostheses 100, 202, or any other prosthesis described herein, is introduced and placed (733) into the implantation space in a collapsed and/or rolled form through the incision in some embodiments. In some embodiments, prostheses 100, 202, or any other prosthesis described herein is introduced (712) covered, at least partially, with a protective sheath or a cannula, which is then withdrawn and removed (734). An outer diameter of the protective sheath may be 10 mm or less, optionally 6 mm or less in some embodiments. In some embodiments, the prosthesis and/or protective sheath and/or introducer is inserted with or followed by a camera or any other imaging device.

The prosthesis is then inflated (735), for example by adding a sufficient amount of filler such as saline thereto, for example as described above as with respect to step 716. In some embodiments, the prosthesis is filled with a sufficient amount of filler X to or over a predetermined or a chosen degree, optionally to over 70% of its maximal inflation volume, optionally 90-100% of its maximal inflation volume. In some embodiments, the prosthesis is then deflated by releasing an amount of filler Y from the implant to a lesser degree, optionally to a final chosen characteristic (e.g., a volume and/or consistency), optionally to less than 70% of its maximum volume, optionally 50-70%, optionally to less than 50% its maximal inflation volume.

In some embodiments, the ratio of X:Y is less than or equal to 10:1. In some embodiments, the ratio of X:Y is less than or equal to 7:1. In some embodiments, the ratio of X:Y is less than or equal to 4:1. In some embodiments, the ratio of X:Y is less than or equal to 2:1. In some embodiments, the ratio of X:Y is less than or equal to 1.5:1. In some embodiments, the ratio of X:Y is less than or equal to 1.3:1. In some embodiments, the ratio of X:Y is less than or equal to 1.2:1. In some embodiments, the ratio of X:Y is less than or equal to 1.1:1.

In some embodiments, deflation occurs by using inflation device 200 (or any other fluid passing means) in a reverse mode. Alternatively or additionally, in some embodiments, pressure regulator means are deployed (736), such as pressure regulating valve 600, allowing filler expulsion or release when the prosthesis is pressurized to over a predetermined pressure such as by articulation of a joint. In some embodiments, the pressure regulating valve 600 is preset to burst at or over a threshold pressure of 1 psi, optionally at or over about 5 psi, optionally at or over 8 psi, optionally at or over 12 psi, optionally at or over 20 psi.

In some embodiments, actual deflation occurs by applying (737) external forces to the fully expanded prosthesis via its surrounding environment (e.g., tissues surrounding and/or supporting the implantation space and/or engage with the prosthesis). In some embodiments, external forces are applied by articulating the shoulder joint or moving the shoulder in a chosen range of motion (ROM) scenario, in a manner that contracts the prosthesis and increases its internal pressure. Such ROM may include a set of maneuvers, some of which may instantly build pressures peaks which are over the predetermined pressure, thereby allowing filler release through pressure regulating valve 600 until the prosthesis inner pressure decreases to under the threshold pressure. The ROMs may be passive in the sense that no intentional or unintentional patient related force and/or muscle tone is actively present but only maneuvers performs by the physician when the patient is anesthetized. In some embodiments, such deflation scheme may be used as the prosthesis is patient-specific calibrated. After prosthesis adjustment, pressure regulating valve 600 is neutralized, deactivated or removed and the prosthesis is sealed (738) in some embodiments. Inflation device 200 is then withdrawn and the incision is closed (739) as known in the art and/or as with respect to step 720 above in some embodiments.

It should be noted that the methods shown and described with respect to FIGS. 7A-B are by way of example only, and that similar methods could be used for implantation of any bursa simulating prosthesis designed for use between soft tissues and other tissues of the body.

Figure 7C:
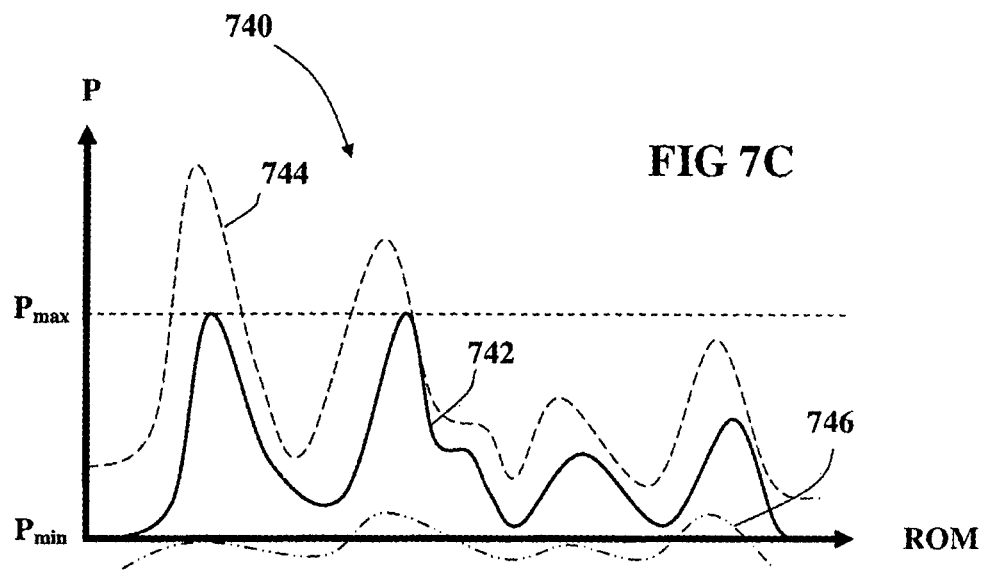
FIG. 7C is a diagram demonstrating pressure-change graphs of a pressure regulated expandable prosthesis versus an over-inflated and an under-inflated expandable prostheses, in accordance with some exemplary embodiments of the invention.

FIG. 7C shows a diagram 740 which is purely schematic and illustrative, demonstrating a pressure-change graph 742 of a prosthesis, such as prostheses 100, 202, or any other prosthesis described herein, which incorporates pressure regulating means such as pressure regulating valve 600, and that is readily implanted using method 730. Graph 742 is presented versus equivalent graphs of identical prostheses being inflated to a chosen degree with no pressure regulation and/or a maximal inflation introductory step: graph 744 of an over-inflated prosthesis and graph 746 of an under-inflated prosthesis. The horizontal axis is set according to the variable ROM maneuvers which may be present as a sequence of prosthesis pressurizations in time, and is referred to as "ROM". The vertical axis presents the variable pressure P that is built in the prostheses in view of the variable ROM. As shown, all graphs include several pressure peaks which present sudden increases of inner pressure due to maximal decrease in volume of the sealed prostheses. Certain movements, e.g. max flexion or extension, may cause highest pressure peaks, although this may be mostly dependent on other patient-specific factors such as the prosthesis surrounding environment (e.g., its consistency, geometry and/or size) and/or its engagement with the prosthesis periphery (e.g., slight over-sizing or under-sizing at nominal positioning, etc). Graph 742 includes max peaks which stop at (or otherwise be only less than) a maximally allowed pressure $P_{max}$ which was set during ROM scenario at step 737 in prosthesis implantation method 730 using valve 600 preset with a threshold pressure substantially same or similar to $P_{max}$. Graph 744 shows the pressurization curve of the over-inflated prosthesis under ROM having two peaks which are over the maximally allowed pressure $P_{max}$. At such pressure peaks, the prosthesis is prone to be compressed and/or contracted to such a degree where its two confronting walls may be too close and even in-contact, an undesired possibility which may cause pain, illness and/or prosthesis failure and misfunction. Moreover, the average inner pressure, including a minimal pressure substantially over $P_{min}$, suggests that the prosthesis is substantially stiffer than desired and therefore may be prone to migrate on certain joint movements. Therefore application of pressure regulating means may ease and/or facilitate boundaries for any expected generated pressure, prosthesis compression and/or possible migration. Graph 746 shows the pressurization curve of the under-inflated prosthesis under ROM: although having no peak which crosses or even come close to maximally allowed pressure $P_{max}$, it is prone to instances in which inner pressure will be less than a minimal value $P_{min}$, especially when no external forces are applied thereto. This way, the prosthesis may not function properly as a spacer, sliding surface and/or a cushion and may even be prone to unstable equilibrium by which certain movements will cause it to permanently shift out of place. This emphasizes an advantage of first inflating the prosthesis to a certain degree higher than a chosen threshold value, and even providing pressure regulating means.

Figure 9:
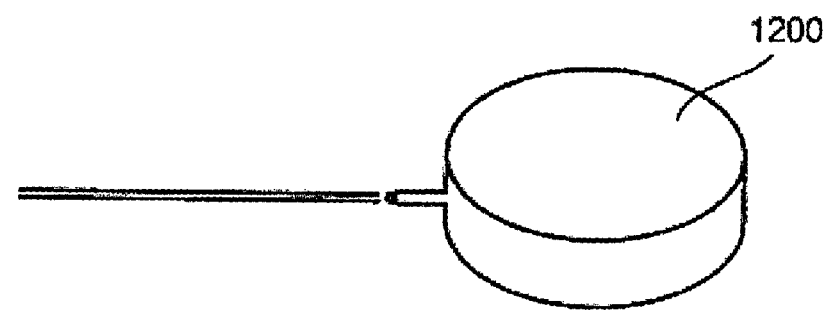
FIG. 9 is a perspective view of a device in accordance with an exemplary embodiment of the invention.

FIG. 9 is a perspective view of a device 1200 in accordance with an exemplary embodiment of the invention. In an embodiment of the invention, device 1200 is a sponge-like structure. In some embodiments of the invention, device 1200 is an inflatable structure. Device 1200 is adapted to be placed at a site in the body for treating inflammation and/or infection, in an embodiment of the invention.

In an exemplary embodiment of the invention, a sponge-like device 1200 is manufactured of biocompatible and/or biodegradable synthetic materials such as, but not limited to, PLA, PLGA, PCL, PDO, poly(lactice acid-co-epsilon caprolactone) or any combination thereof. Alternatively and/or additionally and/or optionally, in some embodiments, the sponge-like device 1200 may be manufactured from biologically derived biodegradable materials such as collagen. Expandable sponge-like device 1200 optionally contains within its cavities at least one biocompatible and/or biodegradable gelling material, such as methyl cellulose, agarose, poly(ethylene-glycol) ("PEG") gel and/or PLA gel, that expands when it comes into contact with at least one bodily fluid, for example by absorbing water. In an embodiment of the invention, such absorption is partly responsible for an expansion of sponge-like device 1200 into its intended deployed position.

As described above, in some exemplary embodiments of the invention, device 1200 comprises an inflatable structure. In an embodiment of the invention, inflatable device 1200 is constructed of at least one biocompatible and/or biodegradable material, such as those described herein. In some embodiments of the invention, inflatable device 1200 is spherical or cylindrical, having a diameter of 0.5 cm to 5 cm for a sphere or in the long direction (x-axis) and 0.5 cm to 4 cm in the short direction (y-axis) and a height (z-axis) of 0.5 mm to 20 mm. In some embodiments of the invention, device 1200 is adapted to be inserted deflated into a patient's body through a cannula. Optionally, the cannula is a 5 mm-7 mm cannula. Optionally, device 1200 dimensions are adapted for a particular intended use.

In some exemplary embodiments, device 1200 is inflated and/or implanted as described herein with respect to prostheses 100 and 202. Device 1200 optionally contains pharmaceutical agents, for example anti-inflammatory drugs and/or antibiotics and/or pro-angiogenesis factors to promote healing, which are eluted into the body. In some embodiments of the invention, device 1200 is adapted to elute pharmaceutical agents according to a predefined schedule. Adaptation of device 1200 includes construction of device 1200 using materials or combinations of materials which degrade at a predetermined rate, thereby releasing pharmaceutical agents contained therein at a predetermined rate. In an exemplary embodiment of the invention, more than one device 1200 is used for treating inflammation and/or infection. Optionally, each device is adapted to elute pharmaceutical agents in view of an overall plan incorporating a plurality of devices.

In another exemplary embodiment of the invention, an expandable device, such as those described herein, is adapted to be used near an articulation to reinforce the articular capsule. In an embodiment of the invention, the expandable device is introduced in anterior fashion to the shoulder articulation between the articular capsule and the deltoid and pectoralis muscle, in order to prevent recurrent dislocation of the shoulder. In another embodiment, the expandable device is introduced in front of the hip joint capsule to prevent anterior dislocation of the hip, especially in cases of congenital dysplasia of hip. In an exemplary embodiment of the invention, the expandable device consists of in inflatable member made of biocompatible and/or biodegradable material. In some embodiments of the invention, the expandable device has a diameter of 1 cm to 10 cm in the long direction (x-axis) and 1 cm to 9 cm in the short direction (y-axis) with a height (z-axis) of 0.5 mm to 25 mm. Optionally, the device has a height of 3 mm to 15 mm.

Figure 10:
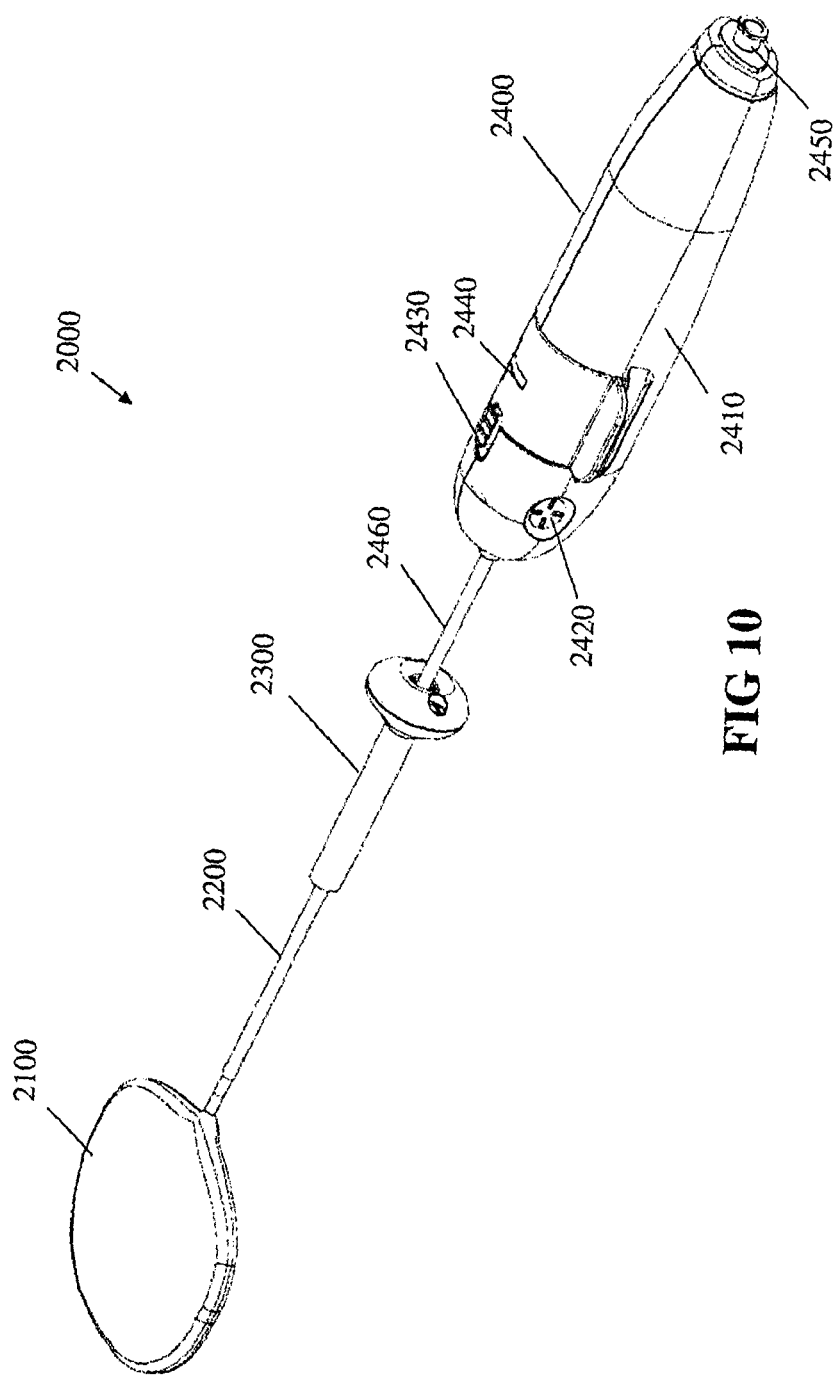
FIG. 10 is an isometric view of a prosthesis implantation and/or inflation device and an inflatable expandable prosthesis, in accordance with an exemplary embodiment of the invention.

Reference is now made to FIG. 10 which shows an isometric view of a prosthesis implantation and/or inflation device 2000 readily connected to an inflatable expandable prosthesis 2100, in accordance with an exemplary embodiment of the invention.

Prosthesis 2100 which is shown fully expanded may be any of the previously described prostheses or may include at least one characteristic thereof. In some embodiments, prosthesis 2100 is an inflatable implant adapted to reach, at a maximal or over a predetermined partial inflation volume, a disc like shape as shown in FIG. 10. As shown, the disc shape generally includes two at least partially parallel and substantially flat, oval surfaces, which are distant one to the other by a relatively small width, and a peripheral, optionally rounded, wall connecting the surfaces while allowing a single port for inflation-deflation. In some embodiments, prosthesis 2100 is manufactured as a single piece, optionally seamless. In some embodiments, prosthesis 2100 consists essentially of a biodegradable material, optionally of a homogenously created wall. In some embodiments, at least one of the flat oval surfaces are smooth enough to allow or even facilitate a continuous unhindered sliding thereon of a tissue in contact, such as a ligament, a tendon, a cartilage or a bone.

In some embodiments, prosthesis 2100 is mounted on a needle 2200 using detachable connection means. Prosthesis 2100 is provided completely deflated and rolled or otherwise collapsed to a small volume for a minimally invasive delivery, while covered, protected and maintained in collapsed form by a sheath 2300. Once in place and before inflation, sheath 2300 is withdrawn thereby allowing prosthesis 2100 to unroll and expand. In some embodiments, during inflation, prosthesis 2100 first unrolls, and only during or after complete unrolling, it begins to expand in width until reaching a fully or predetermine inflated shape or size, for example as shown in FIG. 10.

In some embodiments, prosthesis implantation and/or inflation device 2000 further includes a handheld operator 2400 comprising of housing 2410 ergonomically designed for manual manipulation of needle 2200 and the connected prosthesis 2100 in patient's body.

Operator 2400 includes a knob 2440 that is clock-wise rotatable from a first closed position until a fully opened position, while rotating a tubular stopper 2460 connected thereto over a proximal portion of needle 2200. In some embodiments, needle 2200 includes locking means (not shown) to prosthesis 2100 that are selectively released when stopper 2460 revolves to a partial or full opened position of knob 2440. Alternatively or additionally, clock-wise rotation of knob 2440 promotes axial movement of needle 2200 within tubular stopper 2460 away from prosthesis 2100 until detachment. Optionally, a proximal axial movement further promotes sealing of prosthesis port by forcefully pulling a seal therein. In some embodiments, rotation of knob 2440 is selectively allowed or prevented using safety 2430.

An operator port 2450 located optionally at a proximal end of housing 2410 is connectable to an external inflation medium reservoir and/or pressurizing device, such as a pump or a syringe (not shown). Inflation medium is preferably a fluid (e.g., saline) which is transferable from the external reservoir through a lumen in housing 2410, needle 2200 and into prosthesis 2100.

Needle 2200 and/or stopper 2460 can be made of any biocompatible rigid or semi-rigid material, such as but not limited to metals (e.g., stainless steel). Housing 2410 and other parts affixed thereto can be made of plastic or other polymers such as Polycarbonate. Any of the disclosed parts and elements may be disposable or non-disposable and meant for single or multiple use.

In some embodiments, operator 2400 includes connecting means 2420 to auxiliary devices or instruments, such as a pressure meter, a temperature meter and/or a flow rate meter.

In an exemplary embodiment of the invention, an expandable prosthesis is introduced in a glenohumeral joint capsule between the humerus and glenoid cartilage surfaces, and/or in a subacromial space between a humerus portion and an acromion portion, to prevent injury thereof, or other joint related illness, and/or to permit relatively unhindered or free shoulder movement. Optionally, alternatively and/or additionally, an expandable prosthesis comprises an inflatable structure and a sponge-like structure in combination.

Figure 11:
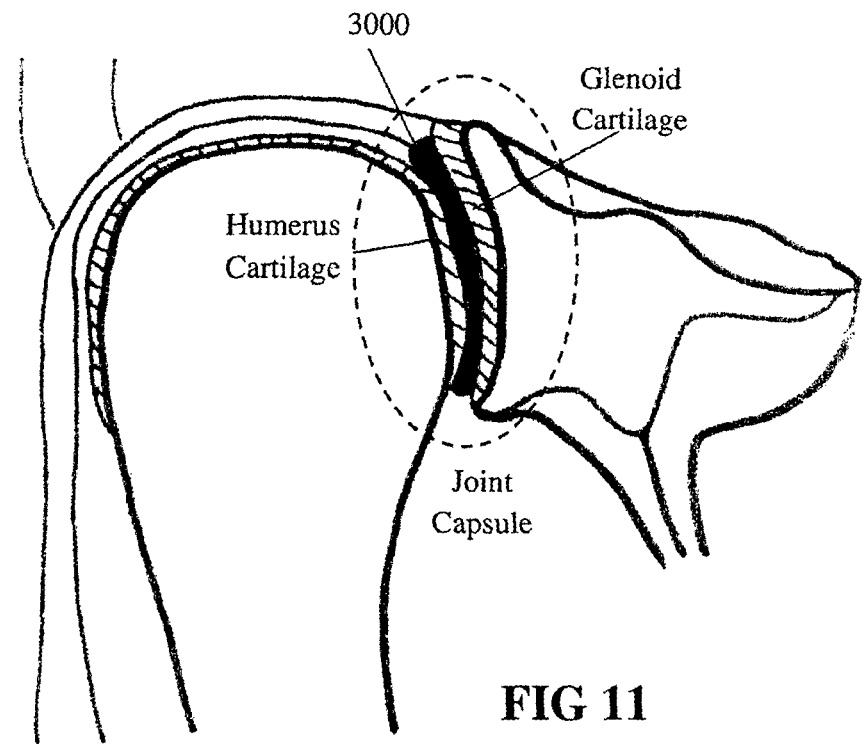
FIG. 11 is a cutaway view of an expandable prosthesis deployed in a glenohumeral joint, in accordance with an exemplary embodiment of the invention.

FIG. 11 is a cutaway view of inflatable expandable prosthesis 3000 deployed in a glenohumeral joint capsule, in accordance with an exemplary embodiment of the invention. In some embodiments, a first surface of prosthesis 3000 is at least occasionally and/or partially in contact with an external surface of a cartilage portion of the humerus head/ball. Alternatively or additionally, a second surface of prosthesis 3000 is at least occasionally and/or partially in contact with an external surface of a glenoid cartilage portion and or with the labrum. In some embodiments, at least one surface of prosthesis 3000 is smooth and allows gliding and/or frictionless motion of a cartilage portion in contact. Alternatively or additionally, at least one surface is coarse and/or comprising a frictional element (e.g., a mesh) thereby avoiding relative motion with respect to a cartilage portion in contact.

In some embodiments, prosthesis 3000 is configured to change its overall consistency to a specific chosen degree. "Consistency" will be considered herein as any property or combination of properties that directly relate to the prosthesis ability to hold and retain its original shape. Consistency may be the element density, softness, firmness, viscosity or any combination thereof. Prosthesis 3000 consistency may be altered by the degree of relative inflation (vol. of actual inflation medium divided by vol. in maximal inflation) and/or by the properties (e.g., viscosity) of the inflation medium. In some embodiments, prosthesis 3000 is deployed in a consistency that is similar, identical or equivalent to that of a synovial membrane or synovium, optionally the ones of the glenohumeral joint. It should be noted that a viscosity of normal synovial fluid is about 1 to 2 inch string (using a string test model: the max stretchable length of a measured fluid drop). Alternatively, the physician may choose another consistency according to need, which may or may not resemble a consistency of a cartilage or a bone.

In some embodiments, prosthesis 3000 is fully inflated so it may be applied to firmly occupy a space, be uncompressible under unyielding forces and/or separate away the two adjacent joint surfaces. In some embodiments, prosthesis 3000 is not fully inflated at end of procedure so it is compressible under inward pressures. In some embodiments, an inflation device and/or prosthesis 3000 are configured and equipped to allow selective inflation/deflation and/or adjustments to a chosen volume and/or relative inflation. In some embodiments, prosthesis 3000 is filled with a filler such as a Newtonian fluid (e.g., water or saline). Alternatively or additionally, the filler includes a non-Newtonian fluid (e.g., hyaluronic acid) having a determined and/or variable viscosity. Alternatively or additionally, the inflation medium includes a lubricating material, either fluidic or non-fluidic, optionally a non-polar fluid such as lipid or oil. In some embodiments, only a minute quantity of material is introduced into prosthesis 3000 inner volume, optionally inefficient as to promote expansion, but still improves frictionless motion capabilities of prosthesis 3000 inner surfaces one with respect to the other. In some embodiments, prosthesis 3000 wall is sized and configured to have a chosen consistency when inflated partially and/or fully, optionally by combining specific wall thickness and wall material.

Figure 12A:
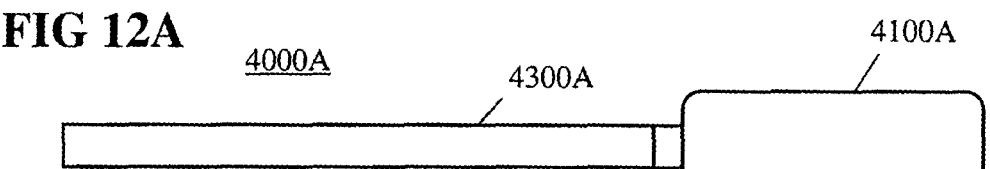
FIGS. 12A-C are schematic cut views of a prosthesis and a portion of an implantation and/or inflation device comprising a pressure regulating valve, in accordance with an exemplary embodiment of the invention.
Figure 12B:
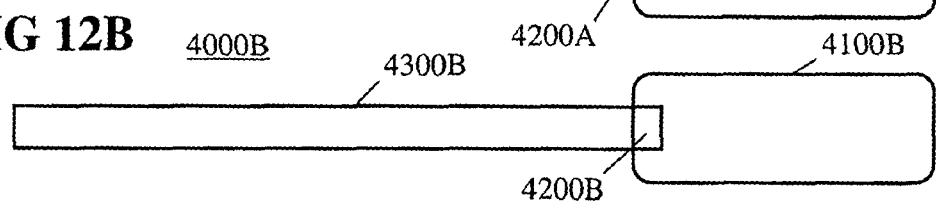
Figure 12C:
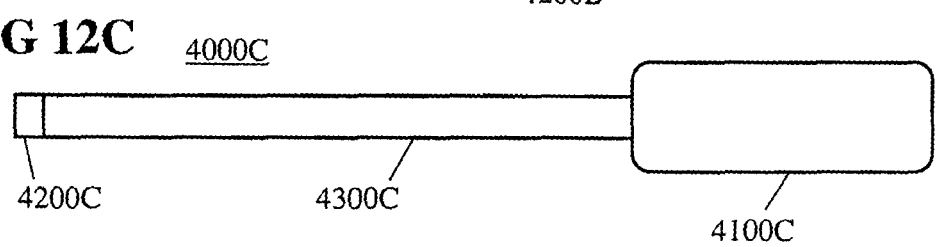

Reference is now made to FIGS. 12A-C which show schematic cut views of prostheses 4000A, 4000B and 4000C, and portions of implantation and/or inflation devices 4300A, 4300B and 4300C, respectively, further comprising pressure regulating valves 4200A, 4200B and 4200C, respectively, at different locations, in accordance with an exemplary embodiment of the invention. The pressure regulating valves are in some embodiments preset or designed to burst or open at a predetermined pressure that is built inside the prostheses. In FIG. 12A, valve 4200A is affixed to a distal end of inflation device 4300A and is releasably attachable to a port of prosthesis 4100A or adjacent releasably attachable connection means on the inflation device. In FIG. 12B, valve 4200B is affixed to a proximal portion of prosthesis 4100B and is releasably attachable to a distal end of inflation device 4300B or adjacent a releasably attachable connection means of the prosthesis. In some embodiments, valve 4200B is made of same materials as prosthesis 4100B and/or is biodegradable. In FIG. 12C, valve 4200C is affixed along the length or at a proximal end of inflation device 4300C and is relatively remote from prosthesis 4100C.

FIGS. 13A-E are schematic cutaway views and an isometric view illustrating deployment stages of prosthesis 4000A between two adjacent joint related tissues, in accordance with an exemplary embodiment of the invention. In some embodiments, the two joint related tissues surround a subacromial space and may include for example ligaments or tendons of a rotator cuff, and/or a humerus, an acromion or a coracoid process. In other embodiments, the two adjacent joint related tissues are bone or cartilage tissues of a synovial joint, for example a humerus tissue and a glenoid tissue in a glenohumeral joint capsule. The following steps will be devoted for subacromial space prosthesis implantation for demonstrative purpose.

In some embodiments, the implant includes a first face and an opposing second face. In some embodiments, the articulation of the joint results in a predetermined distance between the first face and the opposing second face of the implant. In some embodiments, the predetermined distance between the first face and the opposing second face of the implant is greater than 0 millimeters (mm). In some embodiments, the predetermined distance between the first face and the opposing second face of the implant is greater than 0.1 mm, greater than 0.5 mm or greater than 1 mm. In some embodiments, the predetermined distance between the first face and the opposing second face of the implant is sufficient so that the first face and the opposing second face do not touch each other and/or allow unhindered movement there between.

In some embodiments, the predetermined distance between the first face and the opposing second face is a predetermined minimal distance. In some embodiments, the predetermined minimal distance is selected in vivo and/or based on parameters specific to each patient. In some embodiments, the parameters specific to each patient include a maximum pressure reached during ROM. In some embodiments, the maximum pressure reached during ROM is equal to or greater than 1 psi, optionally equal to or greater than 5 psi, optionally equal to or greater than 8 psi, optionally equal to or greater than 12 psi, and/or optionally equal to or greater than 20 psi.

In some embodiments, prior to implantation some patient preparations are performed, for example providing of anxiety reducing medication and/or prophylactic broad spectrum antibiotics. Patient may then be positioned as needed in shoulder surgeries, and surgical procedure begins by firstly accessing the subacromial space using relevant surgical instrumentation (not shown).

Figure 13A:
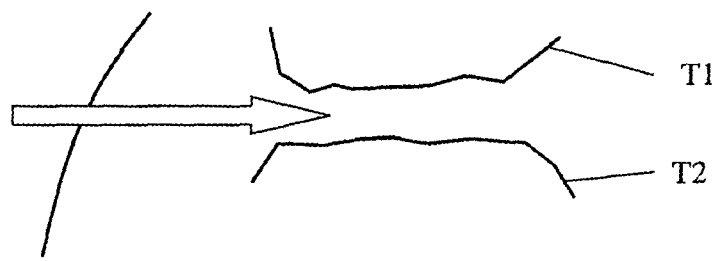
FIGS. 13A-E are schematic cutaway views and an isometric view illustrating deployment stages of a prosthesis between two adjacent joint related tissues, in accordance with an exemplary embodiment of the invention.

Following the routine operational steps measurements of the patient's specific subacromial space are taken, as schematically illustrated in FIG. 13A, for example with a measurement probe such as those which are routinely used in orthopedic surgeries. In some embodiments, the measurements are taken through a true lateral port and optionally include the distance between the lateral Acromion periphery to the superior Glenoid rim.

In some embodiments, a kit comprising a plurality of inflatable prostheses that are differentiated sizes is provided, allowing the surgeon improve fitting to different spaces sized. In some embodiments, the surgeon uses certain correlative keys between subacromial space measurements and provided prostheses sizes, for example: for an acromion-glenoid distance smaller than 5.5 cm, the surgeon is requested to use a "small" sized balloon (for example, having a length of approximately 5 cm or less), for a distance between 5.5 and 6.5 cm, the surgeon is requested to use a "medium" sized prosthesis (for example, a length of approximately 6 cm) and for distance over 6.5 cm the surgeon is requested to a "large" sized prosthesis (for example, a length of approximately 7 cm).

In some embodiments, before or after measurements, the anatomical area of the subacromial space is debrided to a level that enables or improves device implantation. Alternatively or additionally, subacromial space is forcefully increased, for example by pulling away the joint members at a certain direction (as schematically designated by a two sided arrow in FIG. 13B). Alternatively, no change is made to subacromial space size prior to implantation of prosthesis 4000A.

In some embodiments, prior to implantation, prosthesis 4000A is moderately heated and for example is immersed in warm (optionally about 40 degrees Celsius), sterile water thereby becoming more compliant to deployment at bodily temperatures.

Figure 13B:
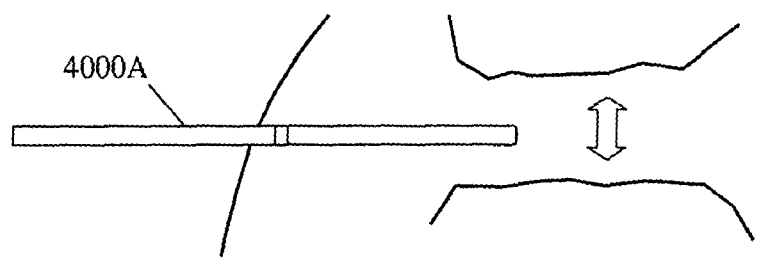
Figure 13C:
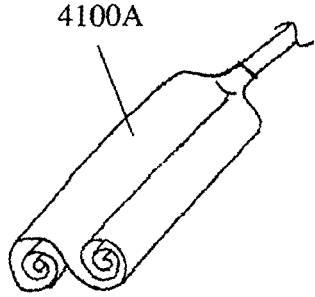

As shown in FIG. 13B, the surgeon then picks a chosen sized prosthesis, in this example prosthesis 4000A, which is provided connected to a delivery and/or inflation device (shown is only a portion thereof). Prosthesis 4000A is inserted through an access port or directly—in case of mini-open and open procedures. In some embodiments, prosthesis 4000A is delivered through a minimally invasive created passage, for example having a cross section diameter of approximately 3 mm or less, therefore is provided fully deflated and collapsed to a small enough size. FIG. 13C shows a partial isometric view of prosthesis 4000A with an exemplary non-binding collapsed form, suggesting a double inward rolling of two opposing prosthesis ends, optionally rolled in opposite directions. In some embodiments, the collapsed prosthesis is delivered enclosed in a dedicated sheath (not, shown) which is withdrawn and removed from site when prosthesis 4000A is properly positioned in the subacromial space.

Next, a syringe prefilled with a sterile saline solution is coupled to the inflation device (not shown) in some embodiments of the invention. In some embodiments, a specific amount of saline is filled and/or is delivered, for example as indicated on the chosen sized prosthesis, optionally by a marking or a label. In some embodiments, prior to syringe filling or prior to delivery, the saline is warmed to approximately 40° C.

Figure 13D:
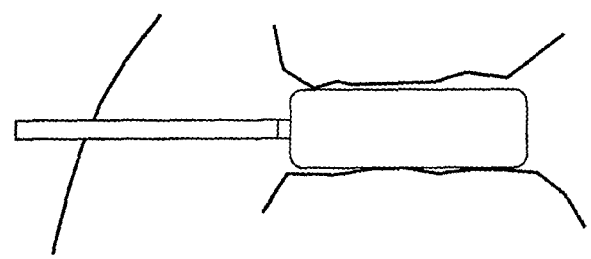

As shown in FIG. 13D, prosthesis 4000A is then inflated to minimal size needed for a full unrolling, optionally to a maximal size and/or a maximally allowed size. Optionally, prosthesis 4000A is inflated until substantially or completely filling the subacromial space, either at rest position (for example when in normal rest size) or at extended position (for example when joint members are forcefully pulled apart). In some embodiments, the prosthesis 4000A is inflated sufficiently to contact at least one surface of the tissue inside the joint or subacromial space. Alternatively, prosthesis 4000A is inflated to an oversized expanded shape which presses or even forcefully increases the subacromial space.

Figure 13E:
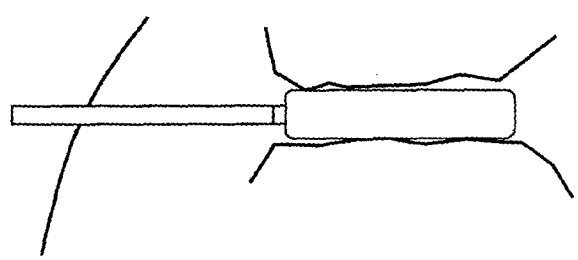

In some embodiments, and as shown in FIG. 13E, prosthesis 4000A is deflated to a smaller size until a requested parameter is met, such as prosthesis internal volume, internal pressure, overall consistency, cushioning degree or another. In some embodiments, deflation is selectively performed. In some embodiment, deflation is performed by actively withdrawing the inflation medium from prosthesis 4000A interior. Alternatively or additionally, deflation occurs passively or actively due to compression forces applied by the two opposing tissues, for example when joint parts falls back into normal position or when deliberate joint movements are done. In some embodiments, deflation is achieved by performing passive (partial or full) range of motion (ROM) of the shoulder.

Such ROMs may include at least one of a forward flexion, an abduction, an external rotation, an internal rotation and/or a cross-body adduction. The ROMs may include series of motions in clockwise and/or counterclockwise directions and may include but not be limited to any of the motions specified above in some embodiments. In some embodiments, deflation occurs actively by withdrawing solution from the prosthesis up to 60-70% the maximal volume (when optionally, a final/optimal volume is confirmed by performing smooth ROM maneuvers).

In some embodiments, prosthesis 4000A is deflated to a chosen internal pressure, optionally predetermined, which may be between 1 and 100 psi, optionally between 1 and 20 psi, optionally between 5 and 10 psi, optionally about 8 psi, or higher, or lower, or any intermediate value. Such deflation may be actively performed, for example by using the syringe in a reverse mode. Alternatively, a pressure regulating valve, which may or may not be unidirectional and settable to deflation, can be preset to burst over a chosen internal pressure. Such a pressure regulating valve may be set either by the prosthesis manufacturer and/or be selectively set by an operator before or during the medical intervention to a predetermined or to a patient-specific value. In some embodiments, the pressure regulating valve may be set to burst at a pressure or at any chosen margin thereof which is equal or associated with a maximal internal pressure which develops in the prosthesis when the treated shoulder is articulated or performs a chosen ROM.

When reaching a chosen volume and/or pressure, the surgeon then operates the prosthesis and/or delivery device to seal the inflation port of prosthesis 4000A and detach it from the inflation device. Alternatively or additionally, deflation is done after prosthesis detachment, for example by performing a full ROM maneuver.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

What is claimed is:

1. A method comprising:
   (a) providing a prosthesis comprising an implant capable of deformation under pressure, the implant including a rigid ring and a lumen therein for enabling filling of the implant;
   (b) inserting the implant in a collapsed state in a void space in a joint as part of an implantation procedure;
   (c) inflating the inserted implant by adding a first amount of a filler to the implant, wherein the first amount of the filler is X;
   (d) after the inserting and inflating, articulating the joint as part of the implantation procedure;
   (e) releasing a second amount of the filler from the implant as part of the implantation procedure, wherein the second amount of the filler released from the implant is Y, and wherein releasing includes releasing the second amount of the filler such that a minimum predetermined distance between opposing sides of the implant is achieved; and
   (f) after the releasing the second amount of the filler, sealing the implant as part of the implantation procedure; wherein X is greater than Y, and wherein sealing the implant includes sliding a plug into the lumen.

2. The method of claim 1, wherein step (d) and step (e) occur concomitantly.

3. The method of claim 1, wherein the implant comprises a first face and an opposing second face, wherein step (d) further comprises articulating the joint to result in a predetermined distance between the first face of the implant and the opposing second face of the implant, wherein the predetermined distance between the first face of the implant and the opposing second face of the implant is greater than 0 millimeters.

4. The method of claim 1, wherein the ratio of X:Y is less than or equal to 4:1.

5. The method of claim 4, wherein the ratio of X:Y is less than or equal to 2:1.

6. The method of claim 1, wherein step (c) causes the implant to fully expand, fully unroll, expand to a predetermined shape, or expand to a predetermined size.

7. The method of claim 1, wherein the joint comprises a shoulder joint.

8. The method of claim 1, wherein step (c) further comprises inflating the implant sufficiently to contact at least one surface of a tissue in the joint.

9. The method of claim 1, wherein articulating the joint comprises a forward flexion, an abduction, an external rotation, an internal rotation or a cross-body adduction.

10. A method comprising:
    (a) providing a prosthesis comprising an implant capable of deformation under pressure, the implant including a rigid ring and a lumen therein for enabling filling of the implant;
    (b) inserting the implant in a void space in a joint;
    (c) inflating the implant by adding a first amount of a filler to the implant, wherein the first amount of the filler is X;
    (d) articulating the joint;
    (e) releasing a second amount of the filler from the implant through a pressure regulating valve based on a predetermined pressure in the implant, wherein the second amount of the filler released from the implant is Y, and, after the releasing, neutralizing, deactivating or removing the pressure regulating valve; and
    (f) sealing the implant after releasing the second amount of the filler, wherein X is greater than Y and wherein sealing the implant includes sliding a plug into the lumen.

11. The method of claim 10, wherein the joint comprises a shoulder joint.

12. The method of claim 10, wherein the implant includes the pressure regulating valve.

13. The method of claim 10, wherein the pressure regulating valve is external from the implant.

14. The method of claim 10, wherein the predetermined pressure in the implant is at least 8 pounds per square inch.

15. The method of claim 10, wherein step (e) further comprises releasing the second amount of the filler from the implant into the void space.

16. The method of claim 10, wherein step (d) and step (e) occur concomitantly.

17. The method of claim 10, wherein the ratio of X:Y is less than or equal to 2:1.

* * * * *